US010386653B2

(12) United States Patent
Beaton et al.

(10) Patent No.: US 10,386,653 B2
(45) Date of Patent: Aug. 20, 2019

(54) VARIABLE OPTIC OPHTHALMIC DEVICE INCLUDING LIQUID CRYSTAL ELEMENTS

(71) Applicant: Johnson & Johnson Vision Care, Inc., Jacksonville, FL (US)

(72) Inventors: Stephen R. Beaton, Jacksonville, FL (US); Luciano De Sio, Winter Park, FL (US); Frederick A. Flitsch, New Windsor, NY (US); Praveen Pandojirao, Jacksonville, FL (US); Randall Braxton Pugh, St. Johns, FL (US); James Daniel Riall, St. Johns, FL (US); Svetlana Serak, Oveido, FL (US); Nelson V. Tabirian, Winter Park, FL (US); Adam Toner, Jacksonville, FL (US); Olena Uskova, Winter Park, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 84 days.

(21) Appl. No.: 15/245,532

(22) Filed: Aug. 24, 2016

(65) Prior Publication Data
US 2016/0363784 A1 Dec. 15, 2016

Related U.S. Application Data

(63) Continuation-in-part of application No. 14/533,657, filed on Nov. 5, 2014, now Pat. No. 9,690,116, which
(Continued)

(51) Int. Cl.
*G02C 7/04* (2006.01)
*G02C 7/08* (2006.01)
*A61F 2/16* (2006.01)

(52) U.S. Cl.
CPC .............. *G02C 7/04* (2013.01); *A61F 2/1627* (2013.01); *A61F 2/1648* (2013.01); *G02C 7/083* (2013.01); *A61F 2250/0002* (2013.01)

(58) Field of Classification Search
None
See application file for complete search history.

(56) References Cited

U.S. PATENT DOCUMENTS 5,682,210 A 10/1997 Weirich
6,120,460 A 9/2000 Abreu
(Continued)

FOREIGN PATENT DOCUMENTS

EP 1783537 A1 5/2007
EP 1947501 A2 7/2008
(Continued)

OTHER PUBLICATIONS

Milton, Harry E. et al., "Electronic Liquid Crystal Contact Lenses for the Correction of Presbyopia", Optics Express, Apr. 7, 2014, vol. 22, No. 7.
(Continued)

*Primary Examiner* — Darryl J Collins
*Assistant Examiner* — Journey F Sumlar

(57) ABSTRACT

Methods and apparatuses for providing a variable optic insert into an ophthalmic lens as set forth. An energy source is capable of powering the variable optic insert included within the ophthalmic lens. In some embodiments, an ophthalmic lens is cast-molded from a silicone hydrogel. The various ophthalmic lens entities may include electroactive liquid crystal layers to electrically control refractive characteristics.

21 Claims, 26 Drawing Sheets

Related U.S. Application Data is a continuation of application No. 13/724,459, filed on Dec. 21, 2012, now Pat. No. 8,906,088, application No. 15/245,532, which is a continuation of application No. 14/469,892, filed on Aug. 27, 2014, now abandoned.

(60) Provisional application No. 61/878,723, filed on Sep. 17, 2013.

(56) References Cited

U.S. PATENT DOCUMENTS

| | | |
|---|---|---|
| 6,312,393 B1 | 11/2001 | Abreu |
| 6,364,482 B1 | 4/2002 | Roffman |
| 6,364,483 B1 | 4/2002 | Grossinger |
| 6,570,386 B2 | 5/2003 | Goldstein |
| 7,018,040 B2 | 3/2006 | Blum |
| 7,169,106 B2 | 1/2007 | Fleischman |
| 7,626,562 B2 | 12/2009 | Iwasaki |
| 7,708,401 B2 | 5/2010 | Sabeta |
| 7,931,832 B2 | 4/2011 | Pugh |
| 8,047,651 B2 | 11/2011 | Blum |
| 8,602,560 B2 | 12/2013 | Marin |
| 8,906,088 B2 | 12/2014 | Pugh |
| 2004/0021929 A1 | 2/2004 | Nishioka |
| 2005/0062679 A1 | 3/2005 | Aharoni |
| 2005/0140924 A1 | 6/2005 | Blum et al. |
| 2005/0151926 A1 | 7/2005 | Kumar |
| 2008/0208335 A1 | 8/2008 | Blum |
| 2008/0278675 A1 | 11/2008 | Escuti |
| 2009/0033863 A1 | 2/2009 | Blum |
| 2009/0076367 A1 | 3/2009 | Sit |
| 2009/0096981 A1 | 4/2009 | Clarke |
| 2009/0244477 A1 | 10/2009 | Pugh |
| 2009/0316097 A1 | 12/2009 | Presniakov |
| 2010/0001926 A1 | 1/2010 | Amirparviz |
| 2010/0072643 A1 | 3/2010 | Pugh |
| 2010/0103368 A1 | 4/2010 | Amirparviz |
| 2010/0103369 A1 | 4/2010 | Pugh |
| 2011/0028807 A1 | 2/2011 | Abreu |
| 2011/0184271 A1 | 7/2011 | Veciana |
| 2011/0188120 A1 | 8/2011 | Tabirian |
| 2011/0262844 A1 | 10/2011 | Tabirian |
| 2012/0140167 A1 | 6/2012 | Blum |
| 2012/0212696 A1 | 8/2012 | Trajkovska |
| 2012/0224127 A1 | 9/2012 | Kwok |
| 2012/0229754 A1 | 9/2012 | Iyer |
| 2013/0050639 A1 | 2/2013 | Trajkovska |
| 2013/0166025 A1 | 6/2013 | Pugh |
| 2013/0208347 A1 | 8/2013 | Haddock |
| 2013/0245754 A1 | 9/2013 | Blum |
| 2014/0036172 A1 | 2/2014 | Trajkovska-Broach |
| 2014/0132904 A1 | 5/2014 | Bos |
| 2014/0327875 A1 | 11/2014 | Blum |
| 2015/0077659 A1 | 3/2015 | Pugh |
| 2015/0077662 A1 | 3/2015 | Pugh |
| 2015/0081016 A1 | 3/2015 | De Sio |
| 2015/0138454 A1 | 5/2015 | Pugh |
| 2016/0062141 A1 | 3/2016 | De Sio |
| 2016/0062146 A1 | 3/2016 | Beaton |

FOREIGN PATENT DOCUMENTS

| | | |
|---|---|---|
| EP | 2063311 A1 | 5/2009 |
| EP | 1783537 A4 | 9/2009 |
| EP | 2431790 A1 | 3/2012 |
| EP | 2602657 A1 | 6/2013 |
| GB | 2493627 A | 2/2013 |
| JP | 11352445 A | 12/1999 |
| JP | 2005115266 A | 4/2005 |
| WO | WO2000049452 A1 | 8/2000 |
| WO | WO2005006035 A1 | 1/2005 |
| WO | WO2006078806 A2 | 7/2006 |
| WO | WO2008091859 A1 | 7/2008 |
| WO | WO2008131329 A1 | 10/2008 |
| WO | WO2009048647 A1 | 4/2009 |
| WO | WO2010036893 A1 | 4/2010 |
| WO | WO2012103497 A1 | 8/2012 |
| WO | WO2012122411 A1 | 9/2012 |
| WO | WO2012170066 A1 | 12/2012 |
| WO | WO2013096781 A1 | 6/2013 |
| WO | WO2013113278 A1 | 8/2013 |

OTHER PUBLICATIONS

Chen, Yuan et al., "High Performance Negative Dielectric Anistrophy Liquid Crystals for Display Applications", Crystals, 2013, 3, 483-503.

Syed, Ishtiaque M. et al., "Novel Switching Mode in a Vertically Aligned Liquid Crystal Contact Lens", Optics Express, Apr. 20, 2015, vol. 23, No. 8.

Ren Hongwen et al., "Tunable Fresnel Lens Using Nanoscale Polymer-Dispersed Liquid Crystals", Applied Physics Letters, American Institute of Physics, vol. 83, No. 8, Aug. 25, 2003, pp. 1515-1517.

Nersisyan S. R. et al., "The Principals of Laser Beam Control with Polarization Gratings Introduced as Diifractive Waeplates", Proceedings of Spie, Spie International Society for Optical Engineering, vol. 7775, Aug. 1, 2010, pp. 77750.

L. Marrucci, et al., "Pancharatnam-Berry phase optical elements for wave front shaping in the visible domain: Switchable helical mode generation", Applied Physics Letters 88, 221102-1, 2006.

Ervin Goldfain, "exact Raytracing Formulae for Parabolic Axial Grin Lenses", Gradient Index, Miniature, and Diffractive Optical Systems, vol. 3778, pp. 2-10.

Asatryan, K., et al., "Optical Lens with Electrically Variable Focus Using an Optically Hidden Dielectric Structure", Optics Express, vol. 18, No. 13, pp. 13981-13992 (2010).

Hoogboom, J., et al., "LCD Alignment Layers, Controlling Nematic Domain Properties", Journal of Material Chemistry, vol. 16, pp. 1305-1314 (2006).

Laude, Vincent, "Twisted-Nematic Liquid-Crystal Pixelatd Active Lens", Optics Communications, vol. 153, pp. 134-152 (1998).

Birefringence in Liquid Crystals, http://plc.cwru.edu/tutorial/enhanced/files/lc/biref.htm, pp. 1-4 Dec. 10, 2012.

De Smet, J. et al., "Design and Wrinkling Behavior of a Contact Lens with an Integrated Liquid Crystal Light Modulator", Journal of Display Technology, May 31, 2012, vol. 8, No. 5, pp. 229-305.

Ren, H. et al., "Tunable-Focus Microlens Arrays using Nanosized Polymer-Dispersed Liquid Crystal Droplets", Optics Communications, Mar. 1, 2005, vol. 247, No. 1-3, pp. 101-106.

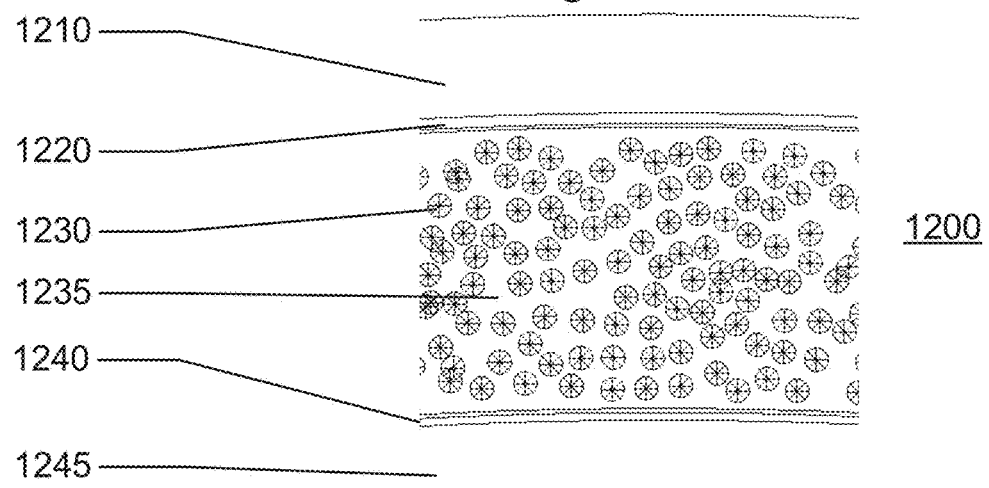
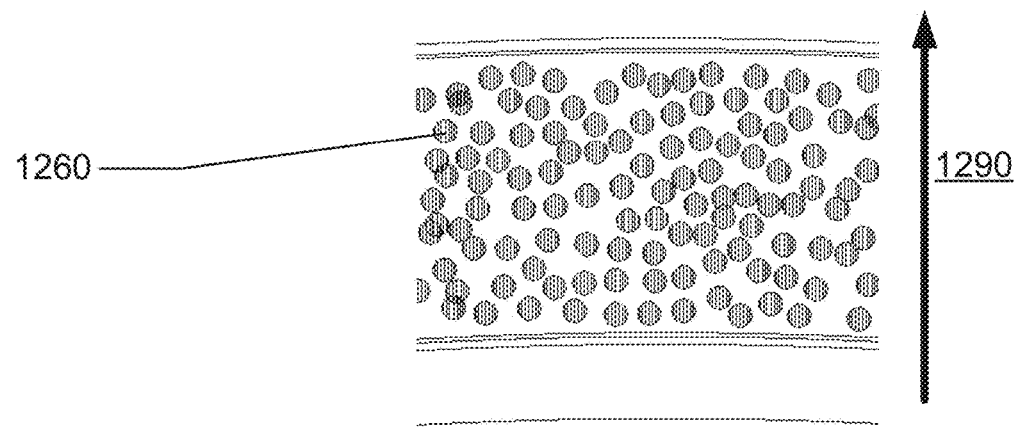

Figure 19A
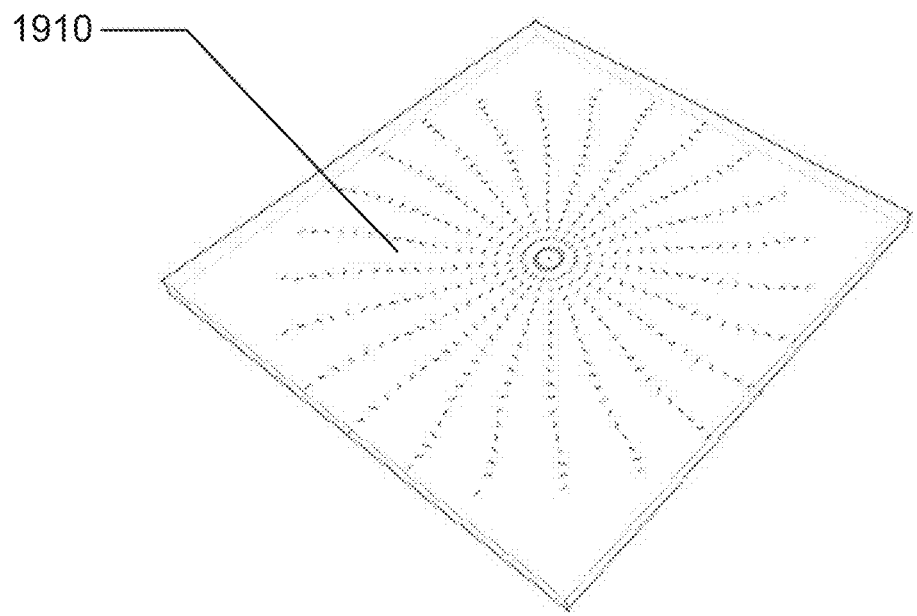
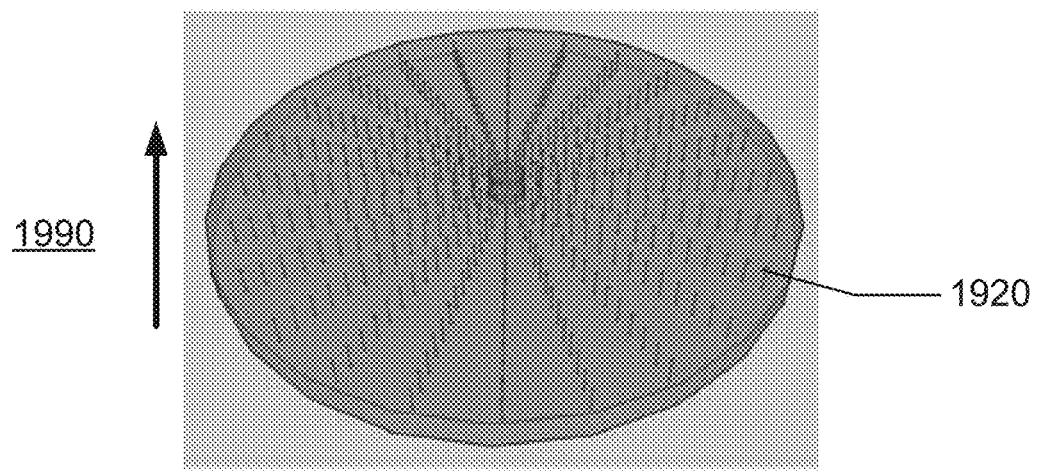
Figure 19B

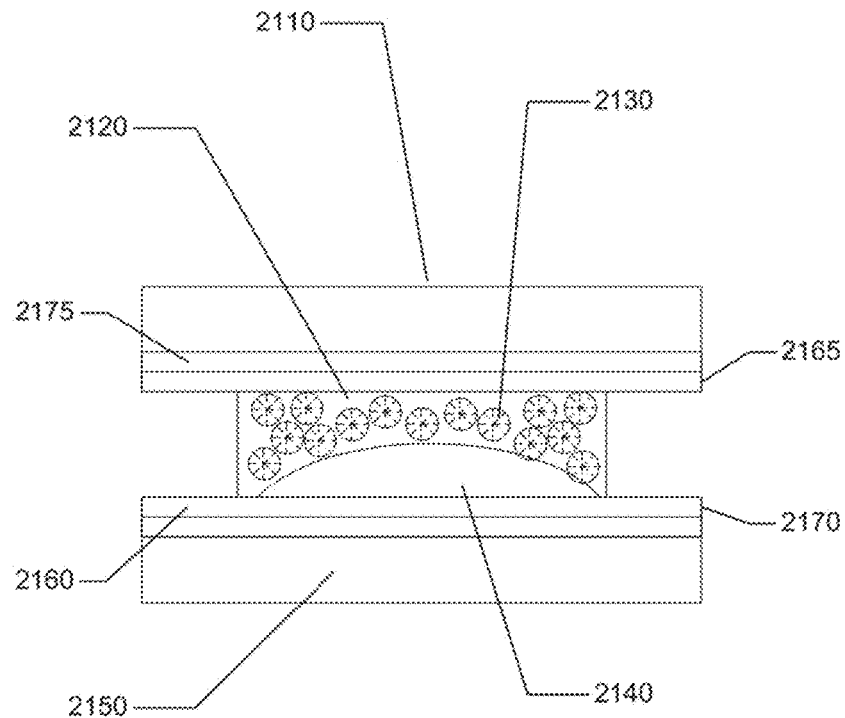
Figure 21
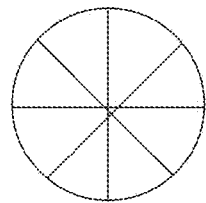 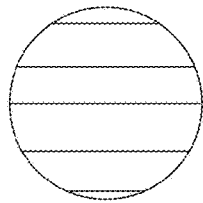 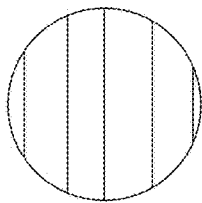 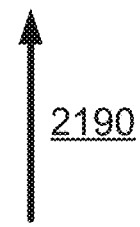
Figure 21A  Figure 21B  Figure 21C

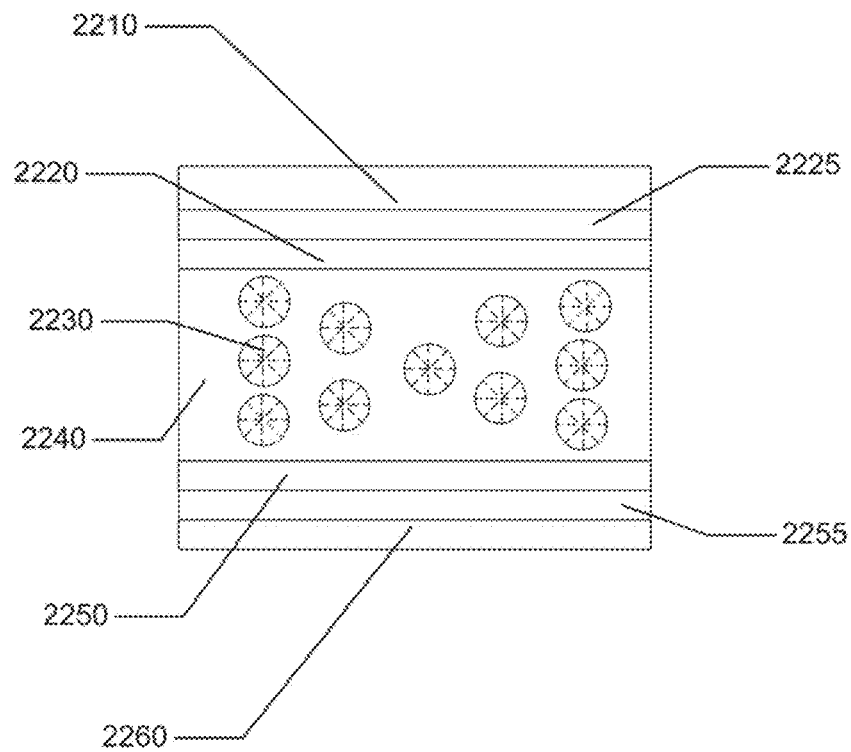
Figure 22
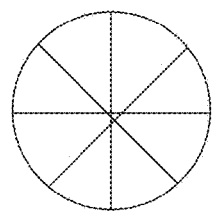 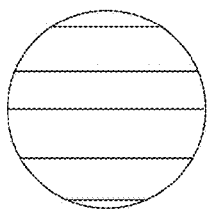 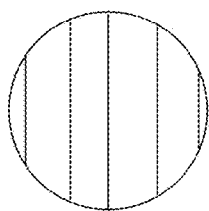 
Figure 22A  Figure 22B  Figure 22C

VARIABLE OPTIC OPHTHALMIC DEVICE INCLUDING LIQUID CRYSTAL ELEMENTS

CROSS REFERENCE TO RELATED APPLICATIONS

This application is a continuation-in-part of U.S. patent application Ser. No. 14/533,657 filed on Nov. 5, 2014 which is a continuation of U.S. patent application Ser. No. 13/724,459 filed on Dec. 21, 2012 (now U.S. Pat. No. 8,906,088) AND a continuation of U.S. patent application Ser. No. 14/469,892 filed on Aug. 27, 2014 which claims the benefit of U.S. Provisional Patent Application No. 61/878,723 filed on Sep. 17, 2013.

BACKGROUND OF THE INVENTION

1. Field of the Invention

The present invention describes an ophthalmic lens device with a variable optic capability and, more specifically, in some embodiments, the fabrication of an ophthalmic lens with a variable optic insert utilizing liquid crystal elements.

2. Discussion of the Related Art

Traditionally an ophthalmic lens, such as a contact lens or an intraocular lens provided a predetermined optical quality. A contact lens, for example, may provide one or more of the following: vision correcting functionality; cosmetic enhancement; and therapeutic effects, but only a set of vision correction functions. Each function is provided by a physical characteristic of the lens. Basically, a design incorporating a refractive quality into a lens provides vision corrective functionality. A pigment incorporated into the lens may provide a cosmetic enhancement. An active agent incorporated into a lens may provide a therapeutic functionality.

To date, optical quality in an ophthalmic lens has been designed into the physical characteristic of the lens. Generally, an optical design has been determined and then imparted into the lens during fabrication of the lens, for example through cast molding, or lathing. The optical qualities of the lens have remained static once the lens has been formed. However, wearers may at times find it beneficial to have more than one focal power available to them in order to provide sight accommodation. Unlike spectacle wearers, who can change spectacles to change an optical correction, contact wearers or those with intraocular lenses have not been able to change the optical characteristics of their vision correction without significant effort.

SUMMARY OF THE INVENTION

Accordingly, the present invention includes innovations relating to a variable optic insert with liquid crystal elements that may be energized and incorporated into an ophthalmic device, which is capable of changing the optical quality of the lens. Examples of such ophthalmic devices may include a contact lens or an intraocular lens. In addition, methods and apparatus for forming an ophthalmic lens with a variable optic insert with liquid crystal elements are presented. Some embodiments may also include a cast-molded silicone hydrogel contact lens with a rigid or formable energized insert, which additionally includes a variable optic portion, wherein the insert is included within the ophthalmic lens in a biocompatible fashion.

The present invention therefore includes disclosure of an ophthalmic lens with a variable optic insert, apparatus for forming an ophthalmic lens with a variable optic insert, and methods for manufacturing the same. An energy source may be deposited onto a variable optic insert and the insert may be placed in proximity to one, or both of, a first mold part and a second mold part. A reactive monomer mixture is placed between the first mold part and the second mold part. The first mold part is positioned proximate to the second mold part thereby forming a lens cavity with the energized media insert and at least some of the reactive monomer mixture in the lens cavity; the reactive monomer mixture is exposed to actinic radiation to form an ophthalmic lens. Lenses are formed via the control of actinic radiation to which the reactive monomer mixture is exposed. In some embodiments, an ophthalmic lens skirt or an insert-encapsulating layer may be comprised of standard hydrogel ophthalmic lens formulations. Exemplary materials with characteristics that may provide an acceptable match to numerous insert materials may include, for example, the Narafilcon family (including Narafilcon A and Narafilcon B), the Etafilcon family (including Etafilcon A), Galyfilcon A and Senofilcon A.

The methods of forming the variable optic insert with liquid crystal elements and the resulting inserts are important aspects of various embodiments. In some embodiments, the liquid crystal may be located between two alignment layers, which may set the resting orientation for the liquid crystal. Those two alignment layers may be in electrical communication with an energy source through electrodes deposited on substrate layers that contain the variable optic portion. The electrodes may be energized through an intermediate interconnect to an energy source or directly through components embedded in the insert.

The energization of the alignment layers may cause a shift in the liquid crystal from a resting orientation to an energized orientation. In embodiments that operate with two levels of energization, on or off, the liquid crystal may only have one energized orientation. In other alternative embodiments, where energization occurs along a scale of energy levels, the liquid crystal may have multiple energized orientations.

The resulting alignment and orientation of the molecules may affect light that passes through the liquid crystal layer thereby causing the variation in the variable optic insert. For example, the alignment and orientation may act with refractive characteristics upon the incident light. Additionally, the effect may include alteration of polarization of the light. Some embodiments may include a variable optic insert wherein energization alters a focal characteristic of the lens.

In some embodiments, a dielectric material may be deposited between an alignment layer and an electrode. Such embodiments may include dielectric material with three-dimensional characteristics such as, for example, a preformed shape. Other embodiments may include a second layer of dielectric material wherein the first layer of dielectric material varies in thickness across the region within the optical zone resulting in a varying electric field across the layer of liquid crystal material. In alternate embodiments, the ophthalmic lens device may include a first layer of dielectric material that may be a composite of two materials with similar optical characteristics and dissimilar low frequency dielectric characteristics.

BRIEF DESCRIPTION OF THE DRAWINGS

The foregoing and other features and advantages of the invention will be apparent from the following, more particular description of preferred embodiments of the invention, as illustrated in the accompanying drawings.

FIGS. 12A-B illustrate an alternative exemplary embodiment of a variable optic insert wherein the variable optic portion may be comprised of liquid crystal.

FIGS. 19A and 19B illustrate an alternative exemplary embodiment of patterning of liquid crystals which may be incorporated into variable optic inserts.

FIGS. 21, 21A, 21B and 21C illustrate an alternative exemplary embodiment of a variable optic insert wherein the variable optic portion may be comprised of liquid crystal.

FIGS. 22, 22A, 22B and 22 C illustrate an alternative exemplary embodiment of a variable optic insert wherein the variable optic portion may be comprised of liquid crystal.

DETAILED DESCRIPTION OF THE INVENTION

Figure 1:
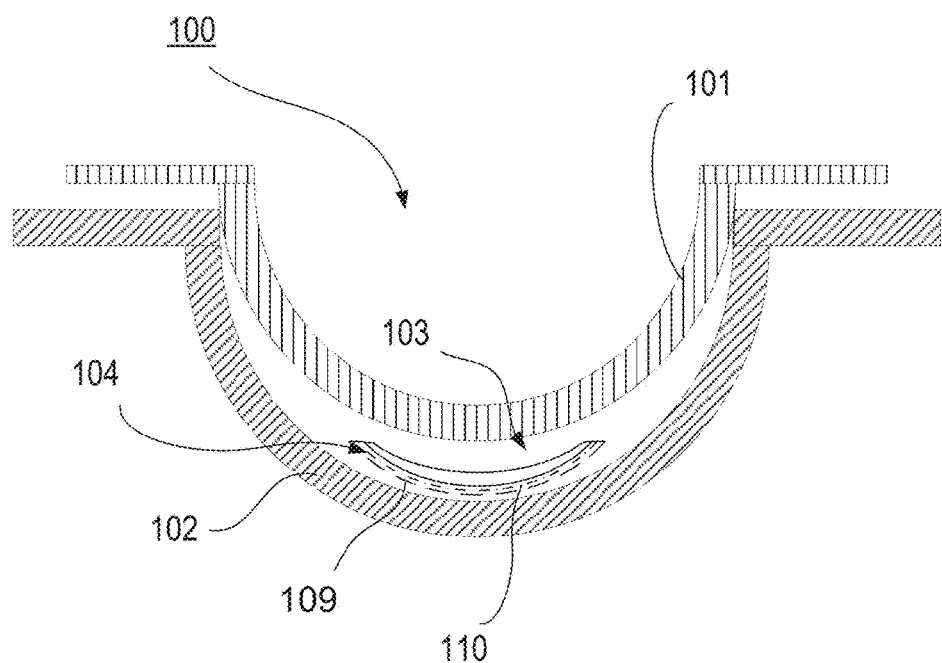
FIG. 1 illustrates exemplary mold assembly apparatus components that may be useful in implementing some embodiments of the present invention.

The present invention includes methods and apparatuses for manufacturing an ophthalmic lens with a variable optic insert wherein the variable optic portion is comprised of a liquid crystal. In addition, the present invention includes an ophthalmic lens with a variable optic insert comprised of liquid crystal incorporated into the ophthalmic lens.

According to the present invention, an ophthalmic lens is formed with an embedded insert and an energy source, such as an electrochemical cell or battery as the storage means for the energy. In some exemplary embodiments, the materials comprising the energy source may be encapsulated and isolated from an environment into which an ophthalmic lens is placed.

A wearer-controlled adjustment device may be used to vary the optic portion. The adjustment device may include, for example, an electronic device or passive device for increasing or decreasing a voltage output. Some exemplary embodiments may also include an automated adjustment device to change the variable optic portion via an automated apparatus according to a measured parameter or a wearer input. Wearer input may include, for example, a switch controlled by wireless apparatus. Wireless may include, for example, radio frequency control, magnetic switching, and inductance switching. In other exemplary embodiments activation may occur in response to a biological function or in response to a measurement of a sensing element within the ophthalmic lens. Other exemplary embodiments may result from the activation being triggered by a change in ambient lighting conditions as a non-limiting example.

In some exemplary embodiments, the insert also includes a variable optic portion comprised of liquid crystal layers. The variation in optic power may occur when electric fields, created by the energization of electrodes, causes realignment within the liquid crystal layer thereby shifting the molecules from the resting orientation to an energized orientation. In other alternative exemplary embodiments, different effects caused by the alteration of liquid crystal layers by energization of electrodes may be exploited, for example, rotation of polarizing angles.

In some exemplary embodiments with liquid crystal layers, there may be elements in the non-optical zone portion of the ophthalmic lens that may be energized, whereas other exemplary embodiments may not require energization. In the embodiments without energization, the liquid crystal may be passively variable based on some exterior factor, for example, ambient temperature, or ambient light.

A liquid crystal lens may provide an electrically variable index of refraction to polarized light incident upon its body. A combination of two lenses where the axis of polarization is rotated in the second lens relative to the first lens allows for a lens element that may be able to vary the index of refraction to ambient non-polarized light.

By combining electrically active liquid crystal layers with electrodes, a physical entity may be achieved that may be controlled by applying an electrical field across the electrodes. If there is a dielectric layer that is present on the periphery of the liquid crystal layer then the field across the dielectric layer and the field across the liquid crystal layer may combine into the field across the electrodes. In a three dimensional shape the nature of the combination of the fields across the layers may be estimated based on electrodynamic principals and the geometry of the dielectric layer and the liquid crystal layer. If the effective electrical thickness of the dielectric layer is made in a non-uniform manner then the effect of a field across the electrodes may be "shaped" by the effective shape of the dielectric and create dimensionally shaped changes in refractive index in the liquid crystal layers. In some exemplary embodiments, such shaping may result in lenses that have the ability to adopt variable focal characteristics.

An alternative exemplary embodiment may derive when the physical lens elements that contain the liquid crystal layers are shaped themselves to have different focal characteristics. The electrically variable index of refraction of a liquid crystal layer may then be used to introduce changes in focal characteristics of the lens based on the application of an electric field across the liquid crystal layer through the use of electrodes. The shape that the front containment surface makes with the liquid crystal layer and the shape that the back containment surface makes with the liquid crystal layer may determine to first order the focal characteristics of the system.

In the following sections, detailed descriptions of exemplary embodiments of the invention will be given. The description of both preferred and alternative embodiments are exemplary embodiments only, and it is understood that to those skilled in the art that variations, modifications and alterations may be apparent. It is therefore to be understood that the exemplary embodiments do not limit the scope of the underlying invention.

Glossary

In this description and claims directed to the presented invention, various terms may be used for which the following definitions will apply:

Alignment layer: as used herein refers to a layer adjacent to a liquid crystal layer that influences and aligns the orientation of molecules within the liquid crystal layer. The resulting alignment and orientation of the molecules may affect light that passes through the liquid crystal layer. For example, the alignment and orientation may act with refractive characteristics upon the incident light. Additionally, the effect may include alteration of polarization of the light.

Electrical Communication: as used herein refers to being influenced by an electrical field. In the case of conductive materials, the influence may result from or in the flow of electrical current. In other materials, it may be an electrical potential field that causes an influence, such as the tendency to orient permanent and induced molecular dipoles along field lines as an example.

Energized: as used herein refers to the state of being able to supply electrical current to or to have electrical energy stored within.

Energized orientation: as used herein refers to the orientation of the molecules of a liquid crystal when influenced by an effect of a potential field powered by an energy source. For example, a device containing liquid crystals may have one energized orientation if the energy source operates as either on or off. In other embodiments, the energized orientation may change along a scale affected by the amount of Energy applied.

Energy: as used herein refers to the capacity of a physical system to do work. Many uses within this invention may relate to the said capacity being able to perform electrical actions in doing work.

Energy source: as used herein refers to device capable of supplying Energy or placing a biomedical device in an Energized state.

Energy Harvesters: as used herein refers to device capable of extracting energy from the environment and convert it to electrical energy.

Intraocular lens: as used herein refers to an ophthalmic lens that is embedded within the eye.

Lens-Forming Mixture or Reactive Mixture or reactive monomer mixture (RMM): as used herein refers to a monomer or prepolymer material that can be cured and cross-linked or crosslinked to form an ophthalmic lens. Various embodiments may include lens-forming mixtures with one or more additives such as: UV blockers, tints, photoinitiators or catalysts, and other additives one might desire in an ophthalmic lens, for example, contact or intraocular lenses.

Lens-Forming Surface: as used herein refers to a surface that is used to mold a lens. In some embodiments, any such surface may have an optical quality surface finish, which indicates that it is sufficiently smooth and formed so that a lens surface fashioned by the polymerization of a lens-forming mixture in contact with the molding surface is optically acceptable. Further, in some embodiments, the lens-forming surface may have a geometry that is necessary to impart to the lens surface the desired optical characteristics, including, for example, spherical, aspherical and cylinder power, wave front aberration correction, and corneal topography correction.

Liquid Crystal: as used herein refers to a state of matter having properties between a conventional liquid and a solid crystal. A liquid crystal cannot be characterized as a solid but its molecules exhibit some degree of alignment. As used herein, a liquid crystal is not limited to a particular phase or structure, but a liquid crystal may have a specific resting orientation. The orientation and phases of a liquid crystal may be manipulated by external forces, for example, temperature, magnetism, or electricity, depending on the class of liquid crystal.

Lithium Ion Cell: as used herein refers to an electrochemical cell where Lithium ions move through the cell to generate electrical energy. This electrochemical cell, typically called a battery, may be reenergized or recharged in its typical forms.

Media insert or insert: as used herein refers to a formable or rigid substrate capable of supporting an energy source within an ophthalmic lens. In some exemplary embodiments, the media insert also includes one or more variable optic portions.

Mold: as used herein refers to a rigid or semi-rigid object that may be used to form lenses from uncured formulations. Some preferred molds include two mold parts forming a front curve mold part and a back curve mold part.

Ophthalmic Lens or Lens: as used herein refers to any ophthalmic device that resides in or on the eye. These devices may provide optical correction or may be cosmetic. For example, the term lens can refer to a contact lens, intraocular lens, overlay lens, ocular insert, optical insert, or other similar device through which vision is corrected or modified, or through which eye physiology is cosmetically enhanced (e.g. iris color) without impeding vision. In some exemplary embodiments, the preferred lenses of the invention are soft contact lenses which are made from silicone elastomers or hydrogels, which include, for example, silicone hydrogels and fluorohydrogels.

Optical zone: as used herein refers to an area of an ophthalmic lens through which a wearer of the ophthalmic lens sees.

Power: as used herein refers to work done or energy transferred per unit of time.

Rechargeable or Reenergizable: as used herein refers to a capability of being restored to a state with higher capacity to do work. Many uses within this invention may relate to the capability of being restored with the ability to flow electrical current at a certain rate for certain, reestablished time period.

Reenergize or Recharge: as used herein refers to the restoration of an energy source to a state with higher capacity to do work. Many uses within this invention may relate to restoring a device to the capability to flow electrical current at a certain rate for a certain, reestablished time period.

Released from a mold: as used herein refers to a lens is either completely separated from the mold, or is only loosely attached so that it can be removed with mild agitation or pushed off with a swab.

Resting orientation: as used herein refers to the orientation of the molecules of a liquid crystal device in its resting, non-energized state.

Variable optic: as used herein refers to the capacity to change an optical quality, such as, for example, the optical power of a lens or the polarizing angle.

Ophthalmic Lenses

Referring to FIG. 1, an apparatus 100 to form ophthalmic devices comprising sealed and encapsulated inserts is depicted. The apparatus includes an exemplary front curve mold 102 and a matching back curve mold 101. A variable optic insert 104 and a body 103 of the ophthalmic device may be located inside the front curve mold 102 and the back curve mold 101. In some exemplary embodiments, the material of the hydrogel body 103 may be a hydrogel material, and the variable optic insert 104 may be surrounded on all surfaces by this material.

The variable optic insert 104 may comprise multiple liquid crystal layers 109 and 110. Other exemplary embodiments may include a single liquid crystal layer, some of which are discussed in later sections. The use of the apparatus 100 may create a novel ophthalmic device comprised of a combination of components with numerous sealed regions.

In some exemplary embodiments, a lens with a variable optic insert 104 may include a rigid center soft skirt design wherein a central rigid optical element including the liquid crystal layers 109 and 110 is in direct contact with the atmosphere and the corneal surface on respective anterior and posterior surfaces. The soft skirt of lens material (typically a hydrogel material) is attached to a periphery of the rigid optical element, and the rigid optical element may also add energy and functionality to the resulting ophthalmic lens.

Figure 2A:
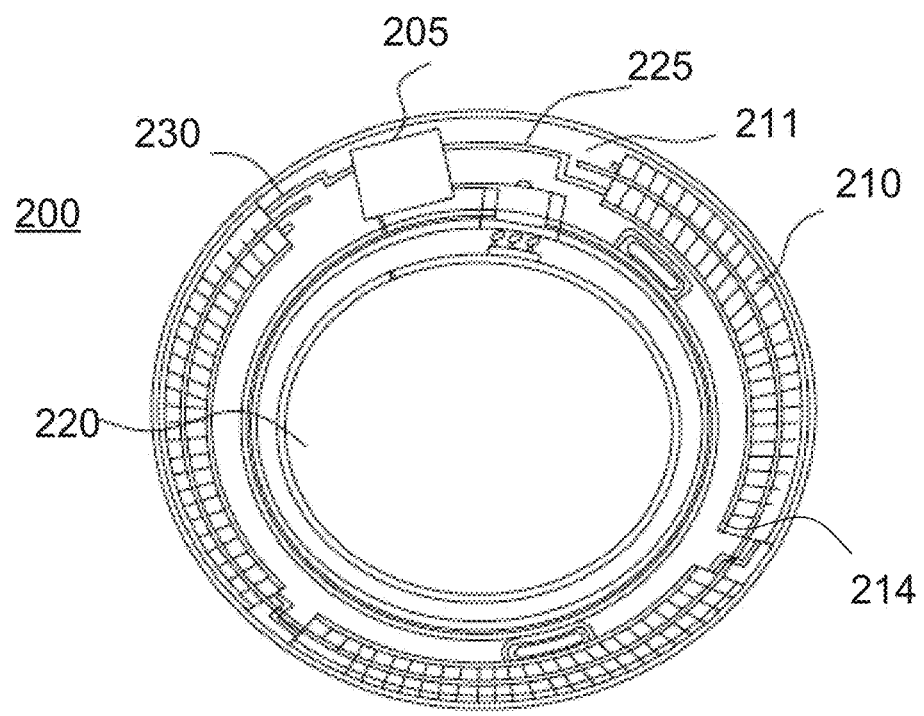
FIGS. 2A and 2B illustrate an exemplary energized ophthalmic lens with a variable optic insert embodiment.
Figure 2B:
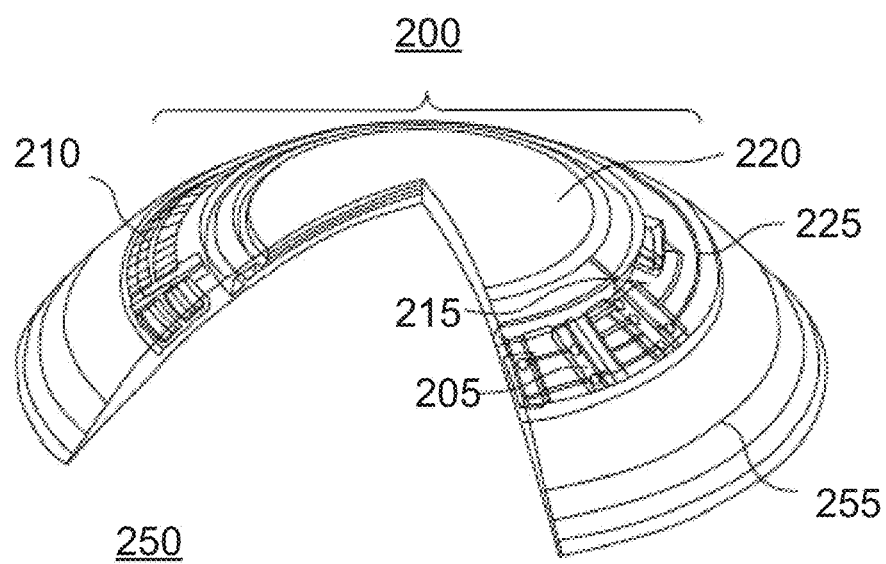

Referring to FIG. 2A, at 200 a top down and FIG. 2B at 250 a cross sectional depiction of an exemplary embodiment of a variable optic insert is shown. In this depiction, an energy source 210 is shown in a periphery portion 211 of the variable optic insert 200. The energy source 210 may include, for example, a thin film, rechargeable lithium ion battery or an alkaline cell based battery. The energy source 210 may be connected to interconnect features 214 to allow for interconnection. Additional interconnects at 225 and 230, for example, may connect the energy source 210 to a circuit such as item 205. In other exemplary embodiments, an insert may have interconnect features deposited on its surface.

In some exemplary embodiments, the variable optic insert 200 may include a flexible substrate. This flexible substrate may be formed into a shape approximating a typical lens form in a similar manner previously discussed or by other means. However to add additional flexibility, the variable optic insert 200 may include additional shape features such as radial cuts along its length. There may be multiple electronic components such as that indicated by 205 such as integrated circuits, discrete components, passive components and such devices that may also be included.

A variable optic portion 220 is also illustrated. The variable optic portion may be varied on command through the application of a current through the variable optic insert. In some exemplary embodiments, the variable optic portion 220 is comprised of a thin layer of liquid crystal between two layers of transparent substrate. There may be numerous manners of electrically activating and controlling the variable optic component, typically through action of the electronic circuit 205. The electronic circuit, may receive signals in various manners and may also connect to sensing elements which may also be in the insert such as item 215. In some embodiments, the variable optic insert may be encapsulated into a lens skirt 255, which may be comprised of hydrogel material or other suitable material to form an ophthalmic lens. In these exemplary embodiments the ophthalmic lens may be comprised of the ophthalmic skirt 255 and an encapsulated ophthalmic lens insert 200 which may itself comprise layers or regions of liquid crystal material or comprising liquid crystal material.

A Variable Optic Insert Including Liquid Crystal Elements

Figure 3:
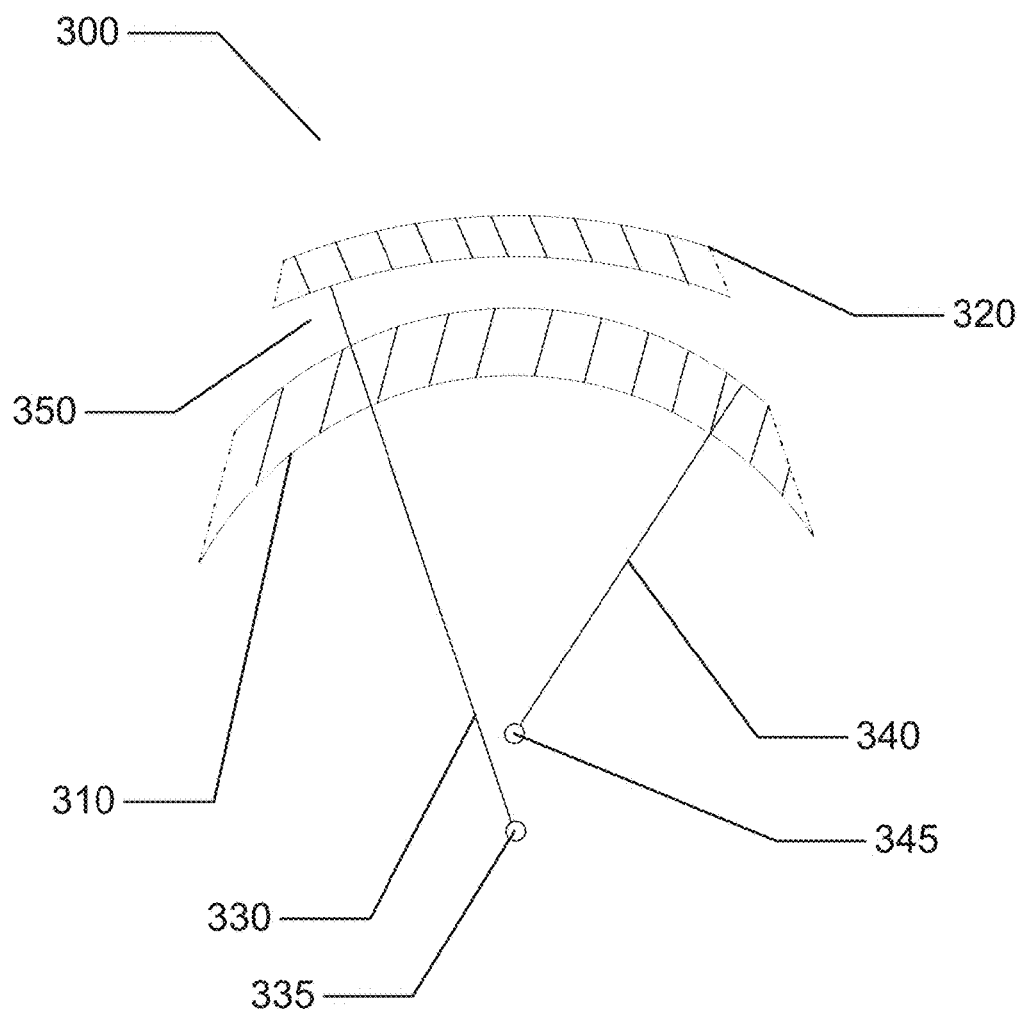
FIG. 3 illustrates a cross sectional view of a variable optic insert where the front and back curve pieces of the variable optic insert may have different curvature and wherein the variable optic portion may be comprised of liquid crystal.

Referring to FIG. 3, item 300, an illustration of the lens effect of two differently shaped lens pieces may be found. As mentioned previously, a variable optic insert of the inventive art herein may be formed by enclosing an electrode and liquid crystal layer system within two differently shaped lens pieces. The electrode and liquid crystal layer system may occupy a space between the lens pieces as illustrated at 350. At 320 a front curve piece may be found and at 310 a rear curve piece may be found.

In a non-limiting example, the front curve piece 320 may have a concave shaped surface that interacts with the space 350. The shape may be further characterized as having a radius of curvature depicted as 330 and a focal point 335 in some embodiments. Other more complicated shapes with various parametric characteristics may be formed within the scope of the inventive art; however, for illustration a simple spherical shape may be depicted.

In a similar and also non-limiting fashion, the back curve piece 310 may have a convex shaped surface that interacts with the space 350. The shape may be further characterized as having a radius of curvature depicted as 340 and a focal point 345 in some embodiments. Other more complicated shapes with various parametric characteristics may be formed within the scope of the inventive art; however, for illustration a simple spherical shape may be depicted.

To illustrate how the lens of the type as 300 may operate, the material that comprises items 310 and 320 may have a natural index of refraction of a predetermined value, within the space 350 the liquid crystal layer may be chosen in a non-limiting example to match that predetermined value for the index of refraction. Thus when light rays traverse the lens pieces 310 and 320 and the space 350, they will not react to the various interfaces in a manner that would adjust the focal characteristics. In its function, portions of the lens not shown may activate an energization of various components that may result in the liquid crystal layer in space 350 assuming a different index of refraction to the incident light ray. In a non-limiting example, the resulting index of refraction may be lowered. Now, at each material interface the path of the light may be modeled to be altered based on the focal characteristics of the surface and the change of the index of refraction.

The model may be based on Snell's law: $\sin(\theta_1)/\sin(\theta_2) = n_2/n_1$. For example, the interface may be formed by piece 320 and space 350. $\theta_1$ may be the angle that the incident ray makes with a surface normal at the interface. $\theta_2$ may be the modeled angle that the ray makes with a surface normal as it leaves the interface. $n_2$ may represent the index of refraction of the space 350 and $n_1$ may represent the index of refraction of the piece 320. When $n_1$ is not equal to $n_2$ then the angles $\theta_1$ and $\theta_2$ will be different as well. Thus, when the electrically variable index of refraction of the liquid crystal layer in space 350 is changed, the path that a light ray would take at the interface will change as well.

Figure 4:
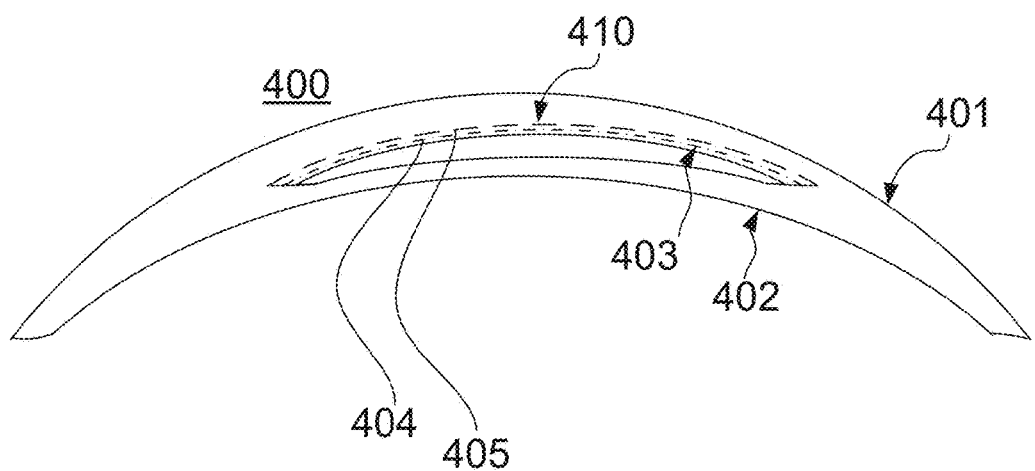
FIG. 4 illustrates a cross sectional view of an ophthalmic lens device embodiment with a variable optic insert wherein the variable optic portion may be comprised of liquid crystal

Referring to FIG. 4, an ophthalmic lens 400 is shown with an embedded variable optic insert 410. The ophthalmic lens 400 may have a front curve surface 401 and a back curve surface 402. The insert 410 may have a variable optic portion 403 with a liquid crystal layer 404. In some exemplary embodiments, the insert 410 may have multiple liquid crystal layers 404 and 405. Portions of the insert 410 may overlap with the optical zone of the ophthalmic lens 400.

Figure 5:
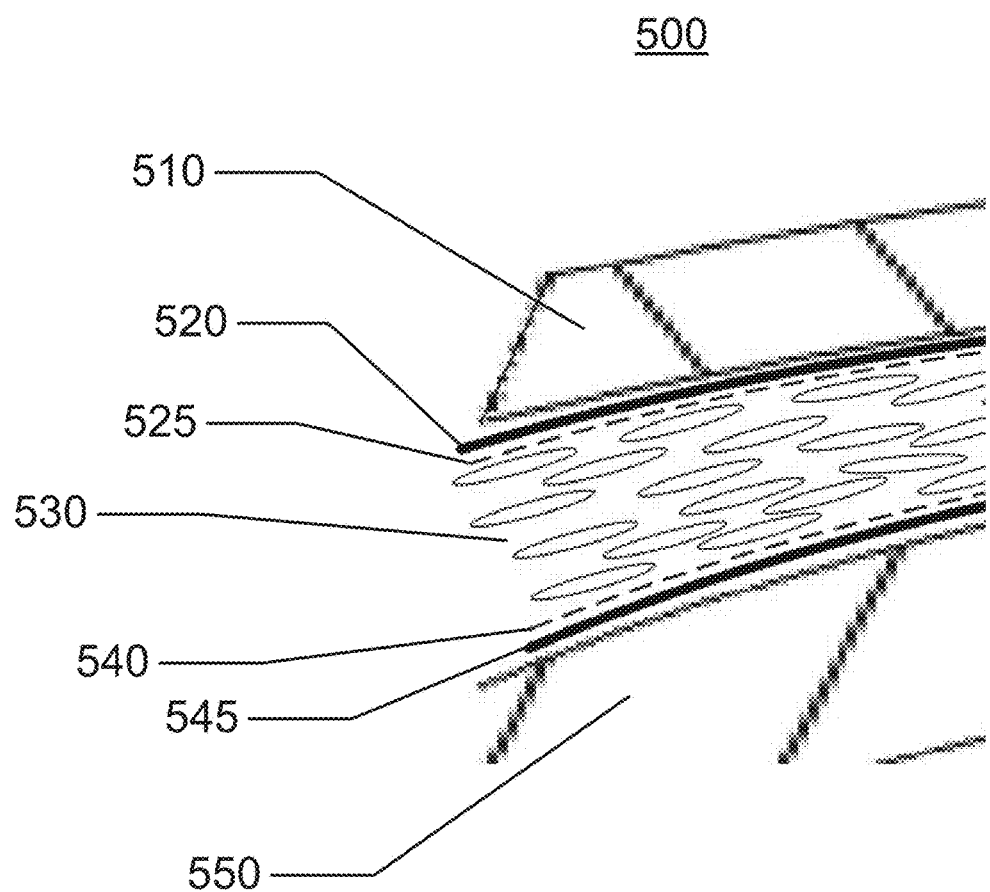
FIG. 5 illustrates an exemplary embodiment or a variable optic insert wherein the variable optic portion may be comprised of liquid crystal.

Referring to FIG. 5, a variable optic portion 500 that may be inserted into an ophthalmic lens is illustrated with a liquid crystal layer 530. The variable optic portion 500 may have a similar diversity of materials and structural relevance as has been discussed in other sections of this specification. In some exemplary embodiments, a transparent electrode 545 may be placed on the first transparent substrate 550. The first lens surface 540 may be comprised of a dielectric film, and in some exemplary embodiments, alignment layers which may be placed upon the first transparent electrode 545. In such exemplary embodiments, the shape of the dielectric layer of the first lens surface 540 may form a regionally varied shape in the dielectric thickness as depicted. Such a regionally varied shape may introduce additional focusing power of the lens element above the geometric effects discussed in reference to FIG. 3. In some embodiments, for example, the shaped layer may be formed by injection molding upon the first transparent electrode 545 substrate 550 combination.

In some exemplary embodiments the first transparent electrode 545 and the second transparent electrode 520 may be shaped in various manners. In some examples, the shaping may result in separate distinct regions being formed that may have energization applied separately. In other examples, the electrodes may be formed into patterns such as a helix from the center of the lens to the periphery which may apply a variable electric field across the liquid crystal layer 530. In either case, such electrode shaping may be performed in addition to the shaping of dielectric layer upon the electrode or instead of such shaping. The shaping of electrodes in these manners may also introduce additional focusing power of the lens element under operation.

A liquid crystal layer 530 may be located between the first transparent electrode 545 and a second transparent electrode 525. The second transparent electrode 525 may be attached to the top substrate layer 510, wherein the device formed from top substrate layer 510 to the bottom substrate layer 550 may comprise the variable optic portion 500 of the ophthalmic lens. Two alignment layers may also be located at 540 and 525 upon the dielectric layer and may surround the liquid crystal layer 525. The alignment layers at 540 and 525 may function to define a resting orientation of the ophthalmic lens. In some exemplary embodiments, the electrode layers 525 and 545 may be in electrical communication with liquid crystal layer 530 and cause a shift in orientation from the resting orientation to at least one energized orientation.

Figure 6:
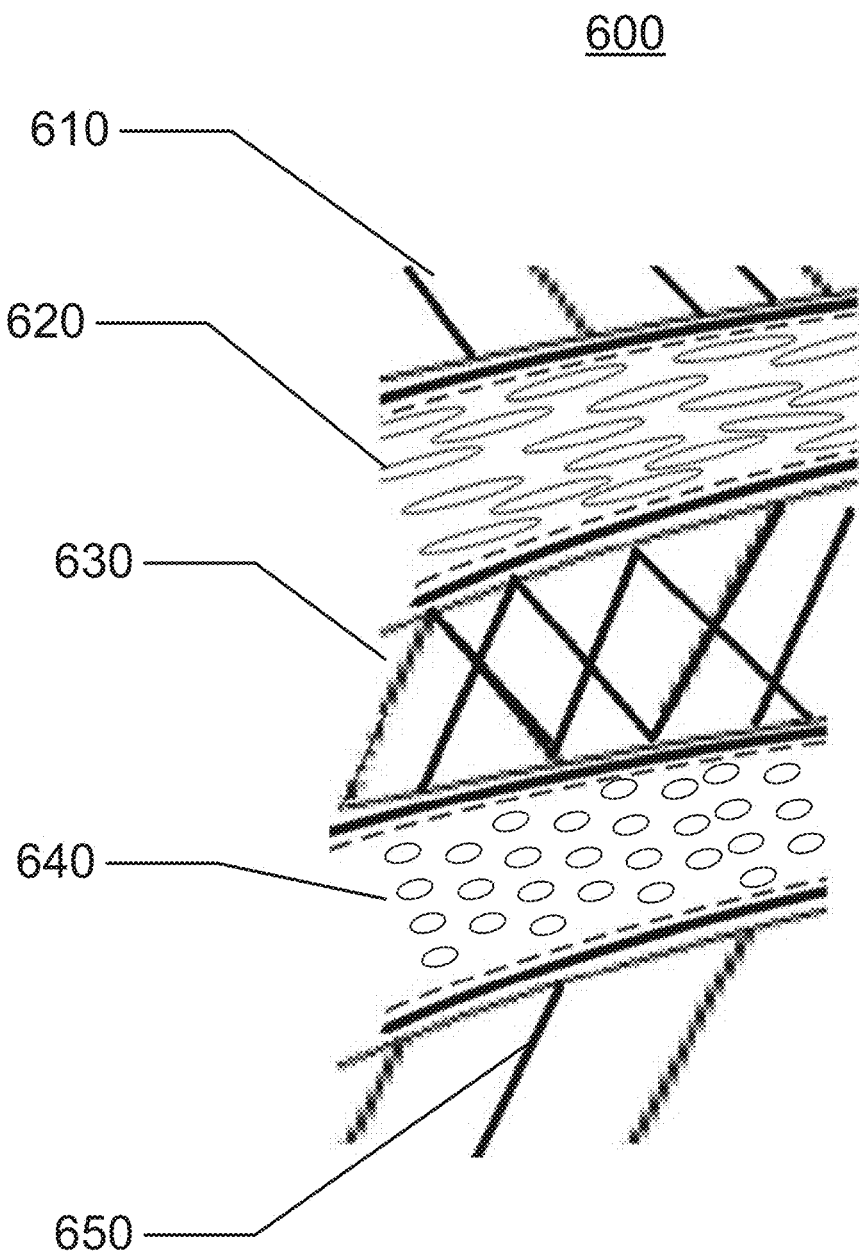
FIG. 6 illustrates an alternative exemplary embodiment of a variable optic insert wherein the variable optic portions may be comprised of liquid crystal.

Referring to FIG. 6, an alternative of a variable optic insert 600 that may be inserted into an ophthalmic lens is illustrated with two liquid crystal layers 620 and 640. Each of the aspects of the various layers around the liquid crystal region may have similar diversity as described in relation to the variable optic insert 500 in FIG. 5. In some exemplary embodiments, the alignment layers may introduce polarization sensitivity into the function of a single liquid crystal element. By combining a first liquid crystal based element formed by a first substrate 610, whose intervening layers in the space around 620 and a second substrate 630 may have a first polarization preference, with a second liquid crystal based element formed by a second surface on the second substrate 630, the intervening layers in the space around 640 and a third substrate 650 with a second polarization preference, a combination may be formed which may allow for an electrically variable focal characteristic of a lens that is not sensitive to the polarization aspects of incident light upon it.

At the exemplary element 600, a combination of two electrically active liquid crystal layers of the various types and diversity associated with the example at 500 may be formed utilizing three substrate layers. In other examples, the device may be formed by the combination of four different substrates. In such examples, the intermediate substrate 630 may be split into two layers. If the substrates are combined at a later time, a device that functions similarly to item 600 may result. The combination of four layers may present a convenient example for the manufacturing of the element where similar devices may be constructed around both 620 and 640 liquid crystal layers where the processing difference may relate to the portion of steps that define alignment features for the liquid crystal element. In still further examples, if the lens element around a single liquid crystal layer such that depicted at 500 is spherically symmetric or symmetric upon a rotation of ninety degrees, then two pieces may be assembled into a structure of the type depicted at 600 by rotating the two pieces ninety degrees relative to each other before assembling.

Materials

Microinjection molding embodiments may include, for example, a poly(4-methylpent-1-ene) copolymer resin are used to form lenses with a diameter of between about 6 mm to 10 mm and a front surface radius of between about 6 mm and 10 mm and a rear surface radius of between about 6 mm and 10 mm and a center thickness of between about 0.050 mm and 1.0 mm. Some exemplary embodiments include an insert with diameter of about 8.9 mm and a front surface radius of about 7.9 mm and a rear surface radius of about 7.8 mm and a center thickness of about 0.200 mm and an edge profile of about 0.050 radius.

The variable optic insert 104 may be placed in a mold part 101 and 102 utilized to form an ophthalmic lens. Mold part 101 and mold part 102 material may include, for example: a polyolefin of one or more of: polypropylene, polystyrene, polyethylene, polymethyl methacrylate, and modified polyolefins. Other molds may include a ceramic or metallic material.

A preferred alicyclic co-polymer contains two different alicyclic polymers. Various grades of alicyclic co-polymers may have glass transition temperatures ranging from 105° C. to 160° C.

In some exemplary embodiments, the molds of the present invention may include polymers such as polypropylene, polyethylene, polystyrene, polymethyl methacrylate, modified polyolefins containing an alicyclic moiety in the main chain and cyclic polyolefins. This blend may be used on either or both mold halves, where it is preferred that this blend is used on the back curve and the front curve consists of the alicyclic co-polymers.

In some preferred methods of making molds 100 according to the present invention, injection molding is utilized according to known techniques, however, exemplary embodiments may also include molds fashioned by other techniques including, for example, lathing, diamond turning, or laser cutting.

Typically, lenses are formed on at least one surface of both mold parts 101 and 102. However, in some exemplary embodiments, one surface of a lens may be formed from a mold part 101 or 102 and another surface of a lens may be formed using a lathing method, or other methods.

In some exemplary embodiments, a preferred lens material includes a silicone containing component. A "silicone-containing component" is one that contains at least one [—Si—O—] unit in a monomer, macromer or prepolymer. Preferably, the total Si and attached O are present in the silicone-containing component in an amount greater than about 20 weight percent, and more preferably greater than 30 weight percent of the total molecular weight of the silicone-containing component. Useful silicone-containing components preferably comprise polymerizable functional groups such as acrylate, methacrylate, acrylamide, methacrylamide, vinyl, N-vinyl lactam, N-vinylamide, and styryl functional groups.

In some exemplary embodiments, the ophthalmic lens skirt, also called an insert-encapsulating layer, that surrounds the insert may be comprised of standard hydrogel ophthalmic lens formulations. Exemplary materials with characteristics that may provide an acceptable match to numerous insert materials may include, but are not limited to, the Narafilcon family (including Narafilcon A and Narafilcon B), and the Etafilcon family (including Etafilcon A). A more technically inclusive discussion follows on the nature of materials consistent with the art herein. One ordinarily skilled in the art may recognize that other material other than those discussed may also form an acceptable enclosure or partial enclosure of the sealed and encapsulated inserts and should be considered consistent and included within the scope of the claims.

Suitable silicone containing components include compounds of Formula I

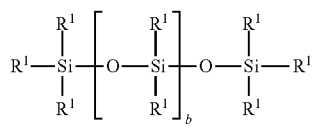

where $R^1$ is independently selected from monovalent reactive groups, monovalent alkyl groups, or monovalent aryl groups, any of the foregoing which may further comprise functionality selected from hydroxy, amino, oxa, carboxy, alkyl carboxy, alkoxy, amido, carbamate, carbonate, halogen or combinations thereof; and monovalent siloxane chains comprising 1-100 Si—O repeat units which may further comprise functionality selected from alkyl, hydroxy, amino, oxa, carboxy, alkyl carboxy, alkoxy, amido, carbamate, halogen or combinations thereof;

where b=0 to 500, where it is understood that when b is other than 0, b is a distribution having a mode equal to a stated value;

wherein at least one $R^1$ comprises a monovalent reactive group, and in some embodiments between one and 3 $R^1$ comprise monovalent reactive groups.

As used herein "monovalent reactive groups" are groups that can undergo free radical and/or cationic polymerization. Non-limiting examples of free radical reactive groups include (meth)acrylates, styryls, vinyls, vinyl ethers, $C_{1-6}$alkyl(meth)acrylates, (meth)acrylamides, $C_{1-6}$alkyl (meth)acrylamides, N-vinyllactams, N-vinylamides, $C_{2-12}$alkenyls, $C_{2-12}$alkenylphenyls, $C_{2-12}$alkenylnaphthyls, $C_{2-6}$alkenylphenyl$C_{1-6}$alkyls, O-vinylcarbamates and O-vinylcarbonates. Non-limiting examples of cationic reactive groups include vinyl ethers or epoxide groups and mixtures thereof. In one embodiment the free radical reactive groups comprises (meth)acrylate, acryloxy, (meth)acrylamide, and mixtures thereof.

Suitable monovalent alkyl and aryl groups include unsubstituted monovalent $C_1$ to $C_{16}$alkyl groups, $C_6$-$C_{14}$ aryl groups, such as substituted and unsubstituted methyl, ethyl, propyl, butyl, 2-hydroxypropyl, propoxypropyl, polyethyleneoxypropyl, combinations thereof and the like.

In one embodiment, b is zero, one $R^1$ is a monovalent reactive group, and at least 3 $R^1$ are selected from monovalent alkyl groups having one to 16 carbon atoms, and in another embodiment from monovalent alkyl groups having one to 6 carbon atoms. Non-limiting examples of silicone components of this embodiment include 2-methyl-,2-hydroxy-3-[3-[1,3,3,3-tetramethyl-1-[(trimethylsilyl)oxy]disiloxanyl]propoxy]propyl ester ("SiGMA"), 2-hydroxy-3-methacryloxypropyloxypropyl-tris(trimethylsiloxy)silane, 3-methacryloxypropyltris(trimethylsiloxy)silane ("TRIS"), 3-methacryloxypropylbis(trimethylsiloxy)methylsilane and 3-methacryloxypropylpentamethyl disiloxane.

In another embodiment, b is 2 to 20, 3 to 15 or in some embodiments 3 to 10; at least one terminal $R^1$ comprises a monovalent reactive group and the remaining $R^1$ are selected from monovalent alkyl groups having 1 to 16 carbon atoms, and in another embodiment from monovalent alkyl groups having 1 to 6 carbon atoms. In yet another embodiment, b is 3 to 15, one terminal $R^1$ comprises a monovalent reactive group, the other terminal $R^1$ comprises a monovalent alkyl group having 1 to 6 carbon atoms and the remaining $R^1$ comprise monovalent alkyl group having 1 to 3 carbon atoms. Non-limiting examples of silicone components of this embodiment include (mono-(2-hydroxy-3-methacryloxypropyl)-propyl ether terminated polydimethylsiloxane (400-1000 MW)) ("OH-mPDMS"), monomethacryloxypropyl terminated mono-n-butyl terminated polydimethylsiloxanes (800-1000 MW), ("mPDMS").

In another embodiment, b is 5 to 400 or from 10 to 300, both terminal $R^1$ comprise monovalent reactive groups and the remaining $R^1$ are independently selected from monovalent alkyl groups having 1 to 18 carbon atoms, which may have ether linkages between carbon atoms and may further comprise halogen.

In one embodiment, where a silicone hydrogel lens is desired, the lens of the present invention will be made from a Reactive Mixture comprising at least about 20 and preferably between about 20 and 70% wt silicone containing components based on total weight of reactive monomer components from which the polymer is made.

In another embodiment, one to four $R^1$ comprises a vinyl carbonate or carbamate of the formula:

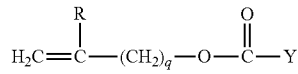

Formula II wherein: Y denotes O—, S— or NH—;
R denotes, hydrogen or methyl; d is 1, 2, 3 or 4; and q is 0 or 1.

The silicone-containing vinyl carbonate or vinyl carbamate monomers specifically include: 1,3-bis[4-(vinyloxycarbonyloxy)but-1-yl]tetramethyl-disiloxane; 3-(vinyloxycarbonylthio) propyl-[tris (trimethylsiloxy)silane]; 3-[tris (trimethylsiloxy)silyl] propyl allyl carbamate; 3-[tris (trimethylsiloxy)silyl] propyl vinyl carbamate; trimethylsilylethyl vinyl carbonate; trimethylsilylmethyl vinyl carbonate, and

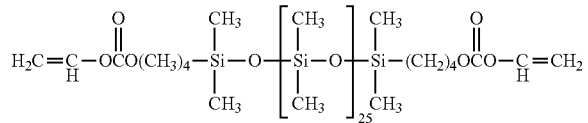

Where biomedical devices with modulus below about 200 are desired, only one $R^1$ shall comprise a monovalent reactive group and no more than two of the remaining $R^1$ groups will comprise monovalent siloxane groups.

Another class of silicone-containing components includes polyurethane macromers of the following formulae:

(*D*A*D*G)$_a$*D*D*E$^1$;

E(*D*G*D*A)$_a$*D*G*D*E$^1$ or;

E(*D*A*D*G)$_a$*D*A*D*E$^1$    Formulae IV-VI wherein:
D denotes an alkyl diradical, an alkyl cycloalkyl diradical, a cycloalkyl diradical, an aryl diradical or an alkylaryl diradical having 6 to 30 carbon atoms,
G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;
* denotes a urethane or ureido linkage;
$a$ is at least 1;
A denotes a divalent polymeric radical of formula:

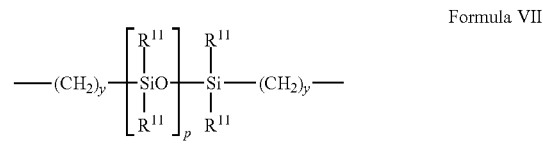

Formula VII $R^{11}$ independently denotes an alkyl or fluoro-substituted alkyl group having 1 to 10 carbon atoms, which may contain ether linkages between carbon atoms; y is at least 1; and p provides a moiety weight of 400 to 10,000; each of E and $E^1$ independently denotes a polymerizable unsaturated organic radical represented by formula:

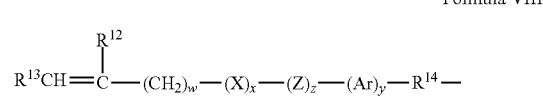

Formula VIII wherein: $R^{12}$ is hydrogen or methyl; $R^{13}$ is hydrogen, an alkyl radical having 1 to 6 carbon atoms, or a —CO—Y—$R^{15}$ radical wherein Y is —O—, Y—S— or —NH—; $R^{14}$ is a divalent radical having 1 to 12 carbon atoms; X denotes —CO— or —OCO—; Z denotes —O— or —NH—; Ar denotes an aromatic radical having 6 to 30 carbon atoms; w is 0 to 6; x is 0 or 1; y is 0 or 1; and z is 0 or 1.

A preferred silicone-containing component is a polyurethane macromer represented by the following formula:

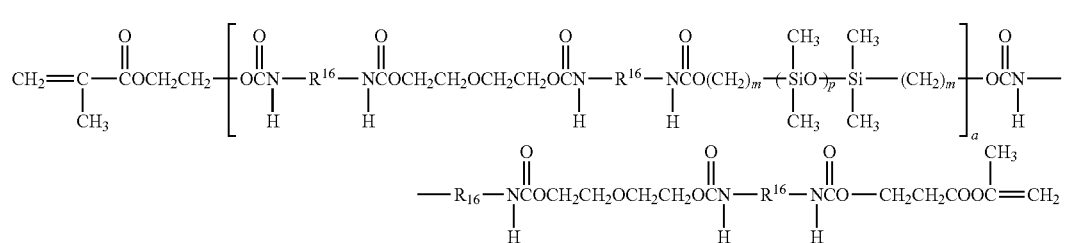

Formula IX wherein $R^{16}$ is a diradical of a diisocyanate after removal of the isocyanate group, such as the diradical of isophorone diisocyanate. Another suitable silicone containing macromer is compound of formula X (in which x+y is a number in the range of 10 to 30) formed by the reaction of fluoroether, hydroxy-terminated polydimethylsiloxane, isophorone diisocyanate and isocyanatoethylmethacrylate.

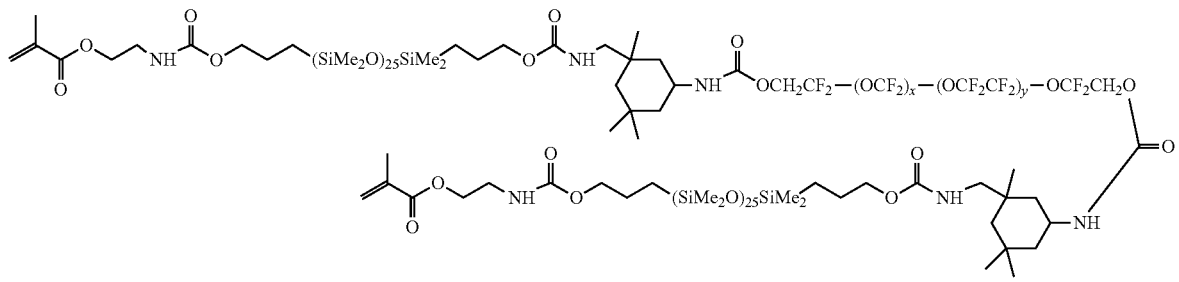

Formula X

Other silicone containing components suitable for use in this invention include macromers containing polysiloxane, polyalkylene ether, diisocyanate, polyfluorinated hydrocarbon, polyfluorinated ether and polysaccharide groups; polysiloxanes with a polar fluorinated graft or side group having a hydrogen atom attached to a terminal difluoro-substituted carbon atom; hydrophilic siloxanyl methacrylates containing ether and siloxanyl linkanges and crosslinkable monomers containing polyether and polysiloxanyl groups. Any of the foregoing polysiloxanes can also be used as the silicone containing component in this invention.

Liquid Crystal Materials

There may be numerous materials that may have characteristics consistent with the liquid crystal layer types that have been discussed herein. It may be expected that liquid crystal materials with favorable toxicity may be preferred and naturally derived cholesteryl based liquid crystal materials may be useful. In other examples, the encapsulation technology and materials of ophthalmic inserts may allow a broad choice of materials that may include the LCD display related materials which may typically be of the broad categories related to nematic or cholesteric N* or smectic C* liquid crystals or liquid crystal mixture. Commercially available mixtures such as Merck Specialty chemicals, Licristal mixtures for TN, VA, PSVA, IPS and FFS applications and other commercially available mixtures may form a material choice to form a liquid crystal layer.

In a non-limiting sense, mixtures or formulations may contain the following liquid crystal materials: 1-(trans-4-Hexylcyclohexyl)-4-isothiocyanatobenzene liquid crystal, benzoic acid compounds including (4-Octylbenzoic acid and 4-Hexylbenzoic acid), carbonitrile compounds including (4'-Pentyl-4-biphenylcarbonitrile, 4'-Octyl-4-biphenylcarbonitrile, 4'-(Octyloxy)-4-biphenylcarbonitrile, 4'-(Hexyloxy)-4-biphenylcarbonitrile, 4-(trans-4-Pentylcyclohexyl)benzonitrile, 4'-(Pentyloxy)-4-biphenylcarbonitrile, 4'-Hexyl-4-biphenylcarbonitrile), and 4,4'-Azoxyanisole.

In a non-limiting sense, a formulation which may be referred to as W1825 may be used as a liquid crystal layer forming material. W1825 may be as available from BEAM Engineering for Advanced Measurements Co. (BEAMCO).

There may be other classes of liquid crystal materials that may be useful for the inventive concepts here. For example, ferroelectric liquid crystals may provide function for electric field oriented liquid crystal embodiments, but may also introduce other effects such as magnetic field interactions. Interactions of electromagnetic radiation with the materials may also differ.

Alignment Layer Materials

In many of the exemplary embodiments that have been described, the liquid crystal layers within ophthalmic lenses may need to be aligned in various manners at insert boundaries. The alignment, for example, may be parallel or perpendicular to the boundaries of the inserts, and this alignment may be obtained by proper processing of the various surfaces. The processing may involve coating the substrates of the inserts that contain the liquid crystal (LC) by alignment layers. Those alignment layers are described herein.

A technique commonly practiced in liquid crystal based devices of various types may be a rubbing technique. These techniques may be adapted to account for the curved surfaces such as the ones of the insert pieces used for enclosing the liquid crystal. In an example, the surfaces may be coated by a Polyvinyl Alcohol (PVA) layer. For example, a PVA layer may be spin coated using a 1 wt. % aqueous solution. The solution may be applied with spin coating at 1000 rpm for time such as approximately 60 s, and then dried. Subsequently, the dried layer may then be rubbed by a soft cloth. In a non-limiting example, the soft cloth may be velvet.

Photo-alignment may be another technique for producing alignment layers upon liquid crystal enclosures. In some exemplary embodiments, photo-alignment may be desirable due to its non-contact nature and the capability of large scale fabrication. In a non-limiting example, the photo-alignment layer used in the liquid crystal variable optic portion may be comprised of a dichroic azobenzene dye (azo dye) capable of aligning predominantly in the direction perpendicular to the polarization of linear polarized light of typically UV wavelengths. Such alignment may be a result of repetitive trans-cis-trans photoisomerization processes.

As an example, PAAD series azobenzene dyes may be spin coated from a 1 wt. % solution in DMF at 3000 rpm for 30 s. Subsequently, the obtained layer may be exposed to a linear polarized light beam of a UV wavelength (such as for example, 325 nm, 351 nm, 365 nm) or even a visible wavelength (400-500 nm). The source of the light may take various forms. In some exemplary embodiments, light may originate from laser sources for example. Other light sources such as LEDs, halogen and incandescent sources may be other non-limiting examples. Either before or after the various forms of light are polarized in the various patterns as appropriate, the light may be collimated in various manners such as through the use of optical lensing devices. Light from a laser source may inherently have a degree of collimation, for example.

A large variety of photoanisotropic materials are known currently, based on azobenzene polymers, polyesthers, photo-crosslinkable polymer liquid crystals with mesogenic 4-(4-methoxycinnamoyloxy)biphenyl side groups and the like. Examples of such materials include sulfonic bisazodye SD1 and other azobenzene dyes, particularly, PAAD-series materials available from BEAM Engineering for Advanced Measurements Co. (BEAMCO), Poly(vinyl cinnamates), and others.

In some exemplary embodiments, it may be desirable to use water or alcohol solutions of PAAD series azo dyes. Some azobenzene dyes, for example, Methyl Red, may be used for photoalignment by directly doping a Liquid Crystal layer. Exposure of the azobenzene dye to a polarized light may cause diffusion and adhesion of the azo dyes to and within the bulk of the liquid crystal layer to the boundary layers creating desired alignment conditions.

Azobenzene dyes such as Methyl Red may also be used in combination with a polymer, for example, PVA. Other photoanisotropic materials capable of enforcing alignment of adjacent layers of liquid crystals may be acceptable are known currently. These examples may include materials based on coumarines, polyesthers, photo-crosslinkable polymer liquid crystals with mesogenic 4-(4-methoxycinnamoyloxy)-biphenyl side groups, Poly(vinyl cinnamates), and others. The photo-alignment technology may be advantageous for embodiments comprising patterned orientation of liquid crystal.

In another exemplary embodiment of producing alignment layers, the alignment layer may be obtained by vacuum deposition of silicon oxide on the insert piece substrates. For example, $SiO_2$ may be deposited at low pressure such as $\sim 10^{-6}$ mbar. It may be possible to provide alignment features at a nanoscaled size that are injection molded into with the creation of the front and back insert pieces. These molded features may be coated in various manners with the materials that have been mentioned or other materials that may directly interact with physical alignment features and transmit the alignment patterning into alignment orientation of liquid crystal molecules.

Still further exemplary embodiments may relate to the creation of physical alignment features to the insert pieces after they are formed. Rubbing techniques as are common in other liquid crystal based art may be performed upon the molded surfaces to create physical grooves. The surfaces may also be subjected to a post molding embossing process to create small grooved features upon them. Still further exemplary embodiments may derive from the use of etching techniques which may involve optical patterning processes of various kinds.

Dielectric Materials

Dielectric films and dielectrics are described herein. By way of non-limiting examples, the dielectric film or dielectrics used in the liquid crystal variable optic portion possess characteristics appropriate to the invention described herein. A dielectric may comprise one or more material layers functioning alone or together as a dielectric. Multiple layers may be used to achieve dielectric performance superior to that of a single dielectric.

The dielectric may permit a defect-free insulating layer at a thickness desired for the discretely variable optic portion, for example, between 1 and 10 μm. A defect may be referred to as a pinhole, as is known by those skilled in the art to be a hole in the dielectric permitting electrical and/or chemical contact through the dielectric. The dielectric, at a given thickness, may meet requirements for breakdown voltage, for example, that the dielectric should withstand 100 volts or more.

The dielectric may allow for fabrication onto curved, conical, spherical, and complex three-dimensional surfaces (e.g., curved surfaces or non-planar surfaces). Typical methods of dip- and spin-coating may be used, or other methods may be employed.

The dielectric may resist damage from chemicals in the variable optic portion, for example, the liquid crystal or liquid crystal mixture, solvents, acids, and bases or other materials that may be present in the formation of the liquid crystal region. The dielectric may resist damage from infrared, ultraviolet, and visible light. Undesirable damage may include degradation to parameters described herein, for example, breakdown voltage and optical transmission. The dielectric may resist permeation of ions. The dielectric may adhere to an underlying electrode and/or substrate, for example, with the use of an adhesion promotion layer. The dielectric may be fabricated using a process which allows for low contamination, low surface defects, conformal coating, and low surface roughness.

The dielectric may possess relative permittivity or a dielectric constant which is compatible with electrical operation of the system, for example, a low relative permittivity to reduce capacitance for a given electrode area. The dielectric may possess high resistivity, thereby permitting a very small current to flow even with high applied voltage. The dielectric may possess qualities desired for an optic device, for example, high transmission, low dispersion, and refractive index within a certain range.

Exemplary, non-limiting, dielectric materials, include one or more of Parylene-C, Parylene-HT, Silicon Dioxide, Silicon Nitride, and Teflon AF.

Electrode Materials

Electrodes are described herein for applying an electric potential for achieving an electric field across the liquid crystal region. An electrode generally comprises one or more material layers functioning alone or together as an electrode.

The electrode may adhere to an underlying substrate, dielectric coating, or other objects in the system, perhaps with the use of an adhesion promoter (e.g., methacryloxypropyltrimethoxysilane). The electrode may form a beneficial native oxide or be processed to create a beneficial oxide layer. The electrode may be transparent, substantially transparent or opaque, with high optical transmission and little reflection. The electrode may be patterned or etched with known processing methods. For example, the electrodes may be evaporated, sputtered, or electroplated, using photolithographic patterning and/or lift-off processes.

The electrode may be designed to have suitable resistivity for use in the electrical system described herein, for example, meeting the requirements for resistance in a given geometric construct.

The electrodes may be manufactured from any suitable material, including one or more of indium tin oxide (ITO), gold, stainless steel, chrome, graphene, graphene doped layers and aluminum. It will be appreciated that this is not an exhaustive list.

Processes

The following method steps are provided as examples of processes that may be implemented according to some aspects of the present invention. It should be understood that the order in which the method steps are presented is not meant to be limiting and other orders may be used to implement the invention. In addition, not all of the steps are required to implement the present invention and additional steps may be included in various exemplary embodiments of the present invention. It may be obvious to one skilled in the art that additional exemplary embodiments may be practical, and such methods are well within the scope of the claims.

Figure 7:
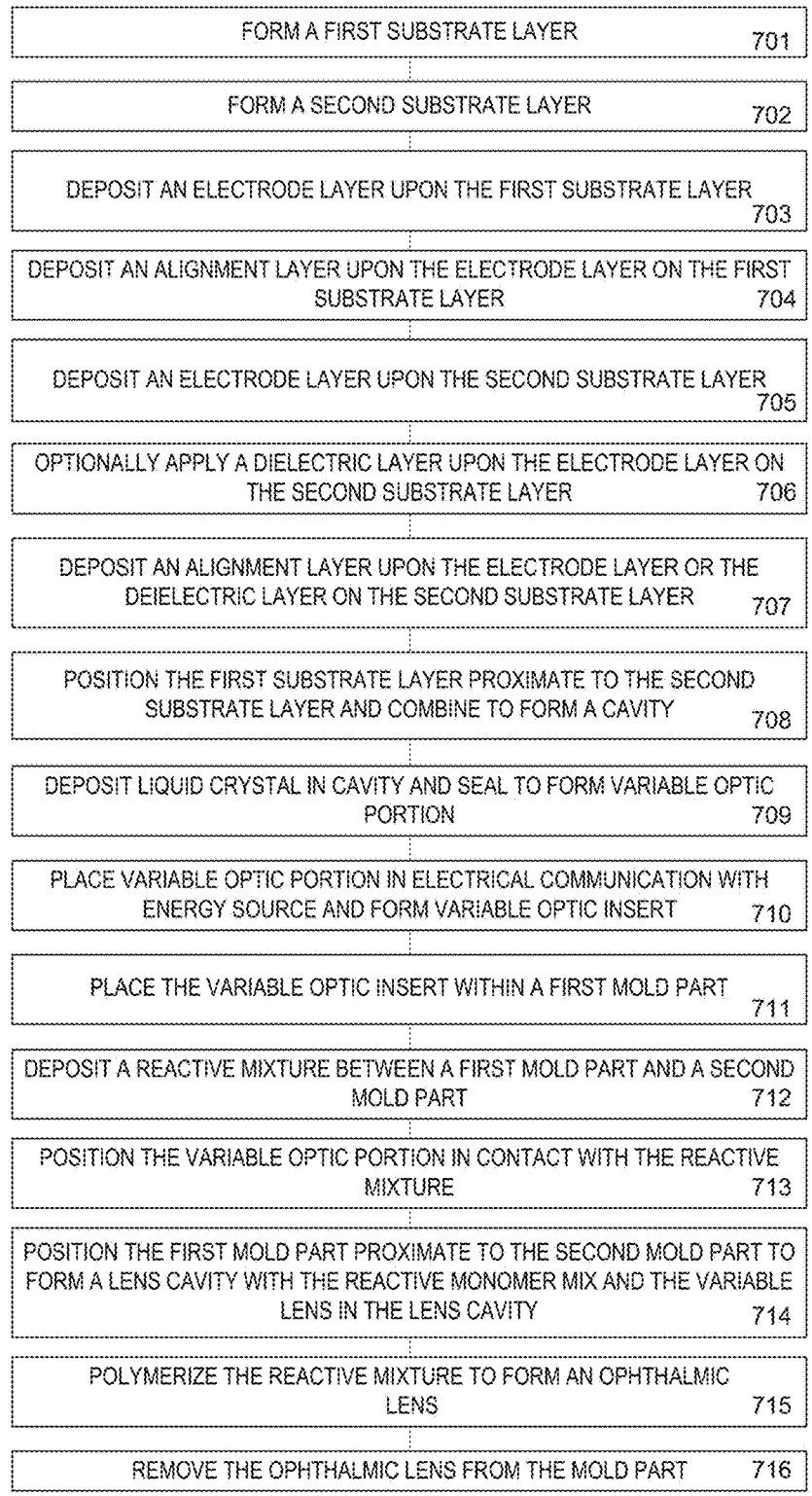
FIG. 7 illustrates method steps for forming an ophthalmic lens with a variable optic insert which may be comprised of liquid crystal.

Referring to FIG. 7, a flowchart illustrates exemplary steps that may be used to implement the present invention. At 701, form a first substrate layer the first substrate layer may comprise a back curve surface and have a top surface with a shape of a first type that may differ from the shape of surface of other substrate layers, and, at 702, form a second substrate layer which may comprise a front curve surface or an intermediate surface or a portion of an intermediate surface for more complicated devices. At 703, an electrode layer may be deposited upon the first substrate layer. The deposition may occur, for example, by vapor deposition or electroplating. In some exemplary embodiments, the first substrate layer may be part of an insert that has regions both in the optical zone and regions in the non-optic zone. The electrode deposition process may simultaneously define interconnect features in some exemplary embodiments.

At 704, the first substrate layer may be further processed to add an alignment layer upon the previously deposited electrode layer. The alignment layers may be deposited upon the top layer on the substrate and then processed in standard manners, for example, rubbing techniques, to create the grooving features that are characteristic of standard alignment layers or by treatment with exposure to energetic particles or light. Thin layers of reactive mesogens may be processed with light exposure to form alignment layers with various characteristics.

At 705, the second substrate layer may be further processed. An electrode layer may be deposited upon the second substrate layer in an analogous fashion to step 703. Then in some exemplary embodiments, at 706, a dielectric layer may be applied upon the second substrate layer upon the electrode layer. The dielectric layer may be formed to have a variable thickness across its surface. As an example, the dielectric layer may be molded upon the first substrate layer. Alternatively, a previously formed dielectric layer may be adhered upon the electrode surface of the second substrate piece.

At 707, an alignment layer may be formed upon the second substrate layer in similar fashion to the processing step at 704. After 707, two separate substrate layers that may form at least a portion of an ophthalmic lens insert may be ready to be joined. In some exemplary embodiments at 708, the two pieces will be brought in close proximity to each other and then liquid crystal material may be filled in between the pieces. At 709, the two pieces may be brought adjacent to each other and then sealed to form a variable optic element with liquid crystal.

In some exemplary embodiments, two pieces of the type formed at 709 may be created by repeating method steps 701 to 709 wherein the alignment layers are offset from each other to allow for a lens that may adjust the focal power of non-polarized light. In such exemplary embodiments, the two variable optic layers may be combined to form a single variable optic insert. At 710, the variable optic portion may be connected to the energy source and intermediate or attached components may be placed thereon.

At 711, the variable optic insert resulting at step 710 may be placed within a mold part. The variable optic insert may or may not also contain one or more components. In some preferred embodiments, the variable optic insert is placed in the mold part via mechanical placement. Mechanical placement may include, for example, a robot or other automation, such as that known in the industry to place surface mount components. Human placement of a variable optic insert is also within the scope of the present invention. Accordingly, any mechanical placement or automation may be utilized which is effective to place a variable optic insert with an energy source within a cast mold part such that the polymerization of a reactive mixture contained by the mold part will include the variable optic in a resultant ophthalmic lens.

In some exemplary embodiments, a variable optic insert is placed in a mold part attached to a substrate. An energy source and one or more components are also attached to the substrate and are in electrical communication with the variable optic insert. Components may include, for example, circuitry to control power applied to the variable optic insert. Accordingly, in some exemplary embodiments a component includes a control mechanism for actuating the variable optic insert to change one or more optical characteristics, for example, a change of state between a first optical power and a second optical power.

In some exemplary embodiments, a processor device, MEMS, NEMS or other component may also be placed into the variable optic insert and in electrical contact with the energy source. At 712, a reactive monomer mixture may be deposited into a mold part. At 713, the variable optic insert may be positioned into contact with the reactive mixture. In some exemplary embodiments the order of placement of variable optic and depositing of monomer mixture may be reversed. At 714, the first mold part is placed proximate to a second mold part to form a lens-forming cavity with at least some of the reactive monomer mixture and the variable optic insert in the cavity. As discussed above, preferred embodiments include an energy source and one or more components also within the cavity and in electrical communication with the variable optic insert.

At 715, the reactive monomer mixture within the cavity is polymerized. Polymerization may be accomplished, for example, via exposure to one or both of actinic radiation and heat. At 716, the ophthalmic lens is removed from the mold parts with the variable optic insert adhered to or encapsulated within the insert-encapsulating polymerized material making up the ophthalmic lens.

Although the invention herein may be used to provide hard or soft contact lenses made of any known lens material, or material suitable for manufacturing such lenses, preferably, the lenses of the invention are soft contact lenses having water contents of about 0 to about 90 percent. More preferably, the lenses are made of monomers containing hydroxy groups, carboxyl groups, or both or be made from silicone-containing polymers, such as siloxanes, hydrogels, silicone hydrogels, and combinations thereof. Material useful for forming the lenses of the invention may be made by reacting blends of macromers, monomers, and combinations thereof along with additives such as polymerization initiators. Suitable materials include, without limitation, silicone hydrogels made from silicone macromers and hydrophilic monomers.

Apparatus

Figure 8:
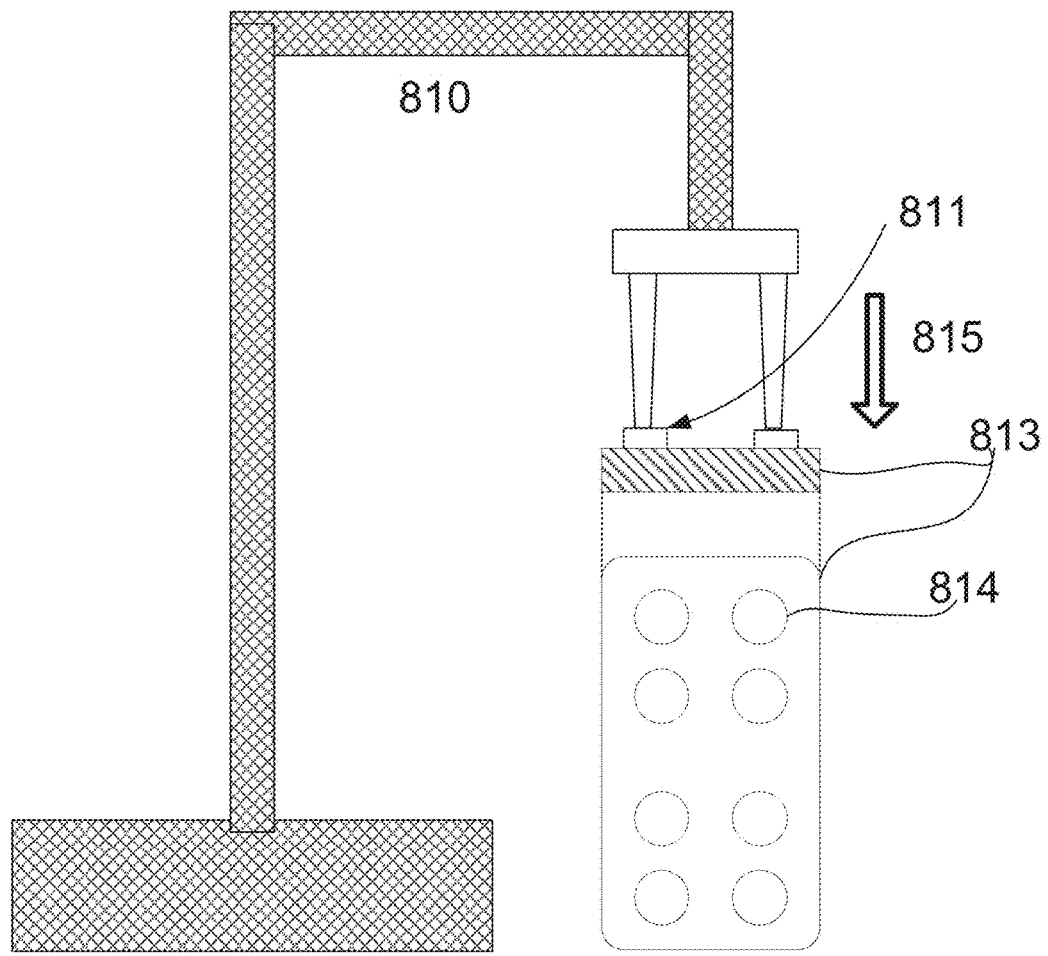
FIG. 8 illustrates an example of apparatus components for placing a variable optic insert comprised of liquid crystal into an ophthalmic lens mold part.

Referring now to FIG. 8, automated apparatus 810 is illustrated with one or more transfer interfaces 811. Multiple mold parts, each with an associated variable optic insert 814 are contained on a pallet 813 and presented to transfer interfaces 811. Embodiments, may include, for example, a single interface individually placing variable optic insert 814, or multiple interfaces (not shown) simultaneously placing variable optic inserts 814 into the multiple mold parts, and in some embodiments, in each mold part. Placement may occur via vertical movement 815 of the transfer interfaces 811.

Another aspect of some embodiments of the present invention includes apparatus to support the variable optic insert 814 while the body of the ophthalmic lens is molded around these components. In some embodiments the variable optic insert 814 and an energy source may affixed to holding points in a lens mold (not illustrated). The holding points may be affixed with polymerized material of the same type that will be formed into the lens body. Other exemplary embodiments include a layer of prepolymer within the mold part onto which the variable optic insert 814 and an energy source may be affixed.

Processors Included in Insert Devices

Figure 9:
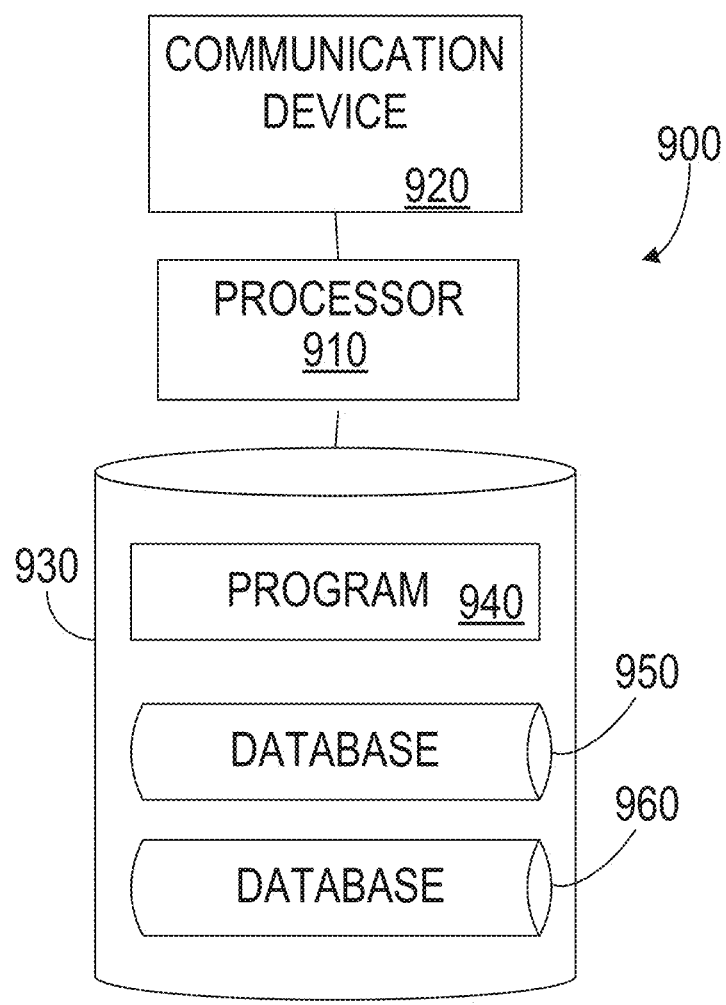
FIG. 9 illustrates a processor that may be used to implement some embodiments of the present invention.

Referring now to FIG. 9, a controller 900 is illustrated that may be used in some exemplary embodiments of the present invention. The controller 900 includes a processor 910, which may include one or more processor components coupled to a communication device 920. In some embodiments, a controller 900 may be used to transmit energy to the energy source placed in the ophthalmic lens.

The controller 900 may include one or more processors, coupled to a communication device configured to communicate energy via a communication channel. The communication device may be used to electronically control one or more of the placement of a variable optic insert into the ophthalmic lens or the transfer of a command to operate a variable optic device.

The communication device 920 may also be used to communicate, for example, with one or more controller apparatus or manufacturing equipment components.

The processor 910 is also in communication with a storage device 930. The storage device 930 may comprise any appropriate information storage device, including combinations of magnetic storage devices (e.g., magnetic tape and hard disk drives), optical storage devices, and/or semiconductor memory devices such as Random Access Memory (RAM) devices and Read Only Memory (ROM) devices.

The storage device 930 may store a program 940 for controlling the processor 910. The processor 910 performs instructions of the program 940, and thereby operates in accordance with the present invention. For example, the processor 910 may receive information descriptive of variable optic insert placement, processing device placement, and the like. The storage device 930 can also store ophthalmic related data in one or more databases 950, 960. The database 950 and 960 may include specific control logic for controlling energy to and from a variable optic lens.

Figure 10:
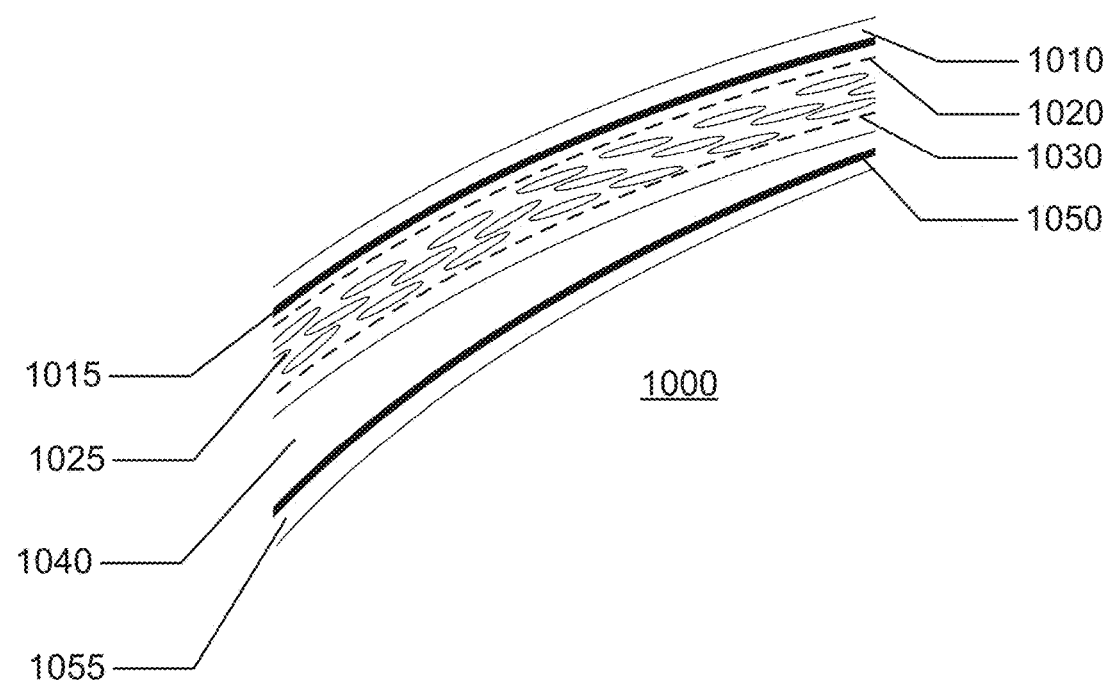
FIG. 10 illustrates an alternative exemplary embodiment of a variable optic insert wherein the variable optic portion may be comprised of liquid crystal.

A Variable Optic Insert Including Liquid Crystal Elements and Shaped Dielectric Layers The various embodiments of liquid crystal materials may be deployed into inserts with shaped insert layers as depicted in FIG. 3. However, an alternative set of exemplary embodiments may be formed using insert pieces that comprise electrodes and shaped dielectric pieces. Referring to FIG. 10, a variable optic portion 1000 that may be inserted into an ophthalmic lens is illustrated with a liquid crystal layer 1025. The variable optic portion 1000 may have a similar diversity of materials and structural relevance as has been discussed in other sections of this specification. In some exemplary embodiments, a transparent electrode 1050 may be placed on the first transparent substrate 1055. The first lens element 1040 may be comprised of a dielectric film, which may be placed upon the first transparent electrode 1050. In such embodiments, the shape of the dielectric layer of the first lens element 1040 may form a regionally varied shape in the dielectric thickness as depicted. In some embodiments, the shaped layer may be formed by injection molding upon the first transparent electrode 1050.

A liquid crystal layer of various types 1025 may be located between the first transparent electrode 1050 and a second transparent electrode 1015. The second transparent electrode 1015 may be attached to the top substrate layer 1010, wherein the device formed from top substrate layer 1010 to the bottom substrate layer 1055 may contain the variable optic portion 1000 of the ophthalmic lens. Two alignment layers 1030 and 1020 may surround the liquid crystal layer 1025. The alignment layers 1030 and 1020 may function to define a resting orientation of the ophthalmic lens. In some exemplary embodiments, the electrode layers 1015 and 1050 may be in electrical communication with liquid crystal layer 1025 and cause a shift in orientation from the resting orientation to at least one energized orientation.

In some exemplary alternative embodiments, the variable optic portion 1000 of an ophthalmic lens may not have alignment layers 1020 and 1030 but instead the transparent electrodes 1015 and 1050 communicate directly with the liquid crystal layer 1025. In such exemplary embodiments, the energization of the liquid crystal layer 1025 may cause a phase change in the liquid crystal thereby changing the optic quality of the variable optic portion 1000 of the ophthalmic lens.

Figure 11:
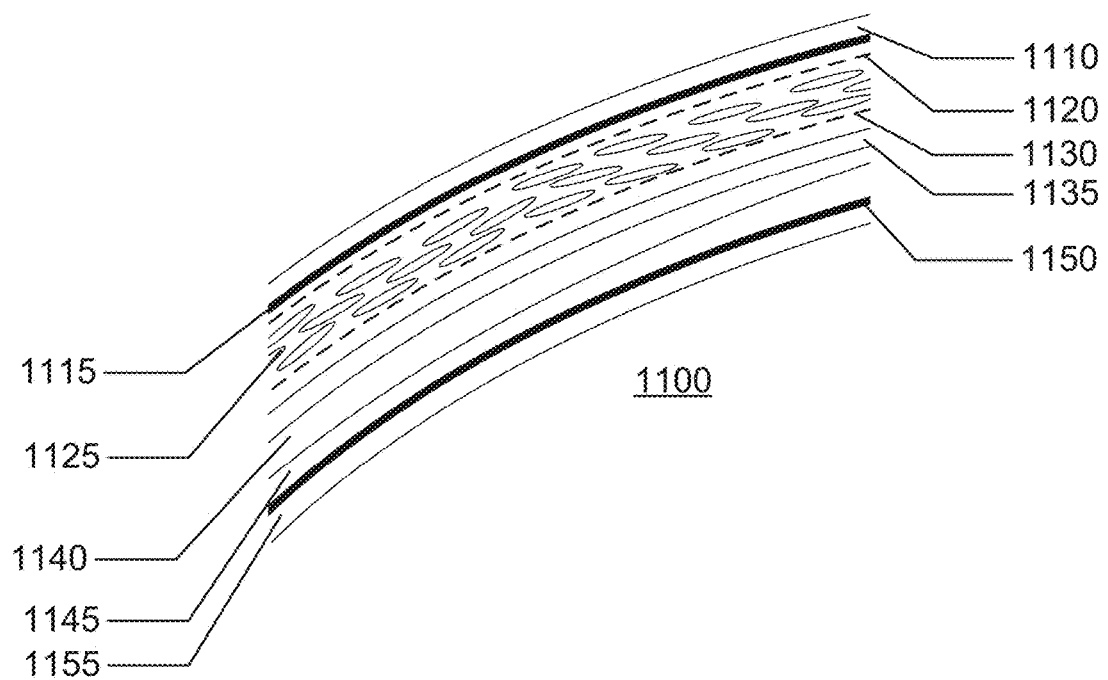
FIG. 11 illustrates an alternative exemplary embodiment of a variable optic insert wherein the variable optic portion may be comprised of liquid crystal.

Referring to FIG. 11, an alternative of a variable optic portion 1100 which may be inserted into an ophthalmic lens is illustrated with a liquid crystal layer 1125. Similar to variable optic portion 1000 in FIG. 10, the layering of substrates 1135 and 1155 and dielectric materials on both the first lens element 1145 and the second lens element 1140 may result in a three-dimensional shape that may affect the optic properties of the liquid crystal layer 1125. A first transparent electrode 1150 may be located on a first substrate layer 1155 of a variable optic portion 1100 of an ophthalmic lens.

Since each layer 1135, 1155, 1145, and 1140 included in the variable optic portion 1100 has a three-dimensional property, the nature of the top substrate layer 1110 and the bottom substrate layer 1155 may be more complex than flat lens embodiments or more typical liquid crystal based embodiments. In some exemplary embodiments, the shape of the top substrate layer 1110 may be different from the bottom substrate layer 1155. Some exemplary embodiments include a first lens element 1145 and a second lens element 1140 both comprised of dielectric material. The second lens element 1140 may have different dielectric properties than the first lens element 1145 at low frequency but may have matched aspects to the first lens element 1145 in an optical spectrum. The materials of the second lens element 1140 may include, for example, aqueous liquids matched to the optical properties of first lens element 1145.

The variable optic portion 1100 may include a median substrate layer 1135 that may form a surface layer upon which the liquid crystal layer 1125 may be deposited. In some exemplary embodiments, the median substrate layer 1135 may also act to contain the second lens element 1140 if said second lens element 1140 is in liquid form. Some exemplary embodiments may include a liquid crystal layer 1125 located between a first alignment layer 1130 and a second alignment layer 1120 wherein the second alignment layer 1120 is placed upon a second transparent electrode 1115. A top substrate layer 1110 may comprise the combination of layers that form the variable optic portion 1100, which may respond to electrical fields applied across its electrodes 1150 and 1115. The alignment layers 1120 and 1130 may affect the optical characteristics of the variable optic portion 1100 by various means.

Liquid Crystal Devices Comprising Nano Sized Polymer Dispersed Liquid Crystal Layers Referring to FIGS. 12A and 12B, a variable optic portion FIG. 12A that may be inserted into an ophthalmic lens is illustrated with a polymer layer 1235 and a nano-sized polymer dispersed liquid crystal droplets illustrated at numerous locations, for example, 1230. The polymerized regions may give the film structural definition and shape while the droplets, such as 1230, rich in liquid crystal material may have a significant optical effect on light transmitting through the layer.

The nano-sized droplets are useful in that they are small enough in dimension that the altered refractive index between the droplets and neighboring layers both in energized and non-energized states may not be significant in terms of scattering processes.

The confinement of the liquid crystals to nano-sized droplets may make it more difficult for molecules to rotate within the droplet. This effect may result in larger electric fields being used to align the liquid crystal molecules into an energized state. As well, the engineering of the chemical structures of the liquid crystal molecules may also help to define conditions that allow for lower electrical fields being required for establishing aligned states.

There may be numerous manners to form a polymer dispersed liquid crystal layer of the type illustrated at 1200. In a first example, a mixture of a monomer and a liquid crystal molecule may be formed with the combination being heated to form an homogenous mixture. Next, the mixture may be applied to a front curve insert piece 1210 and then encapsulated in the lens insert by the addition of a back curve or intermediate insert piece 1245. The insert comprising the liquid crystal mixture may then be cooled at a controlled and predetermined rate. As the mixture cools, regions of relatively pure liquid crystal monomer may precipitate as droplets or droplets within the layer. A subsequent processing step to catalyze polymerization of the monomer may then be performed. In some examples, actinic radiation may be shown on the mixture to initiate polymerization.

In another example, a mixture of liquid crystal and liquid crystal monomer may also be performed. In this example, the mixture may be applied to a front curve piece 1210 or a rear or intermediate curve piece 1245 and then the additional piece may be applied. The applied mixture may already comprise components to trigger the polymerization reactions. Or, actinic radiation may be directed upon the mixture to initiate polymerization. With certain material choices for the monomer and initiating agents, the polymerization reaction may proceed at a rate and in such a manner that high concentration regions of liquid crystal monomer that are similar to droplets or droplets within the polymerized network of material may be formed. These droplets may be surrounded by polymerized material that also comprises an amount of liquid crystal molecules. These liquid crystal molecules may be free to move within the polymer matrix before it is fully polymerized and may also be able to feel orienting effects in their neighboring regions which may be other liquid crystal molecules or alignment features on the surfaces of the insert pieces that the liquid crystal mixture was applied to. The alignment regions may determine a resting state for the liquid crystal molecules within the polymer matrix and may determine a fixed orientation of the liquid crystal molecules in the polymerized regions after significant polymerization has occurred. As well, the aligned liquid crystal molecules in the polymer may also exert an orienting effect on the liquid crystal molecules within droplets or droplets of liquid crystal molecules. Thus, the layer of combined polymerized regions and included droplet regions may exist in a natural alignment state predetermined by the inclusion of alignment features upon the insert pieces before the insert is formed with the liquid crystal intermediate layer.

There may be numerous manners to incorporate liquid crystal molecules into the polymerized or gelled regions. In the previous descriptions some manners have been described. Nevertheless, any method of creating polymer dispersed liquid crystal layers may comprise art within the scope of the present invention and may be used to create an ophthalmic device. The previous examples mentioned the use of monomers to create polymerized layers that surround droplets of liquid crystal molecules. The state of the polymerized monomers may be a crystalline form of polymerized material, or in other embodiments may also exist as a gelled form of polymerized monomer.

The variable optic portion in FIG. 12A may have other aspects that may be defined by a similar diversity of materials and structural relevance as has been discussed in other sections of this specification. In some exemplary embodiments, a transparent electrode 1220 may be placed on the first transparent substrate 1210. The first lens surface may be comprised of a dielectric film, and in some exemplary embodiments, alignment layers which may be placed upon the first transparent electrode 1220. In such exemplary embodiments, the shape of the dielectric layer of the first lens surface may form a regionally varied shape in the dielectric thickness. Such a regionally varied shape may introduce additional focusing power of the lens element above the geometric effects discussed in reference to FIG. 3. In some exemplary embodiments, for example, the shaped layer may be formed by injection molding upon the first transparent electrode 1220 substrate 1210 combination.

In some exemplary embodiments the first transparent electrode 1220 and the second transparent electrode 1240 may be shaped in various manners. In some examples, the shaping may result in separate distinct regions being formed that may have energization applied separately. In other examples, the electrodes may be formed into patterns such as a helix from the center of the lens to the periphery which may apply a variable electric field across the liquid crystal layer 1230 and 1235. In either case, such electrode shaping may be performed in addition to the shaping of dielectric layers upon the electrode or instead of such shaping. The shaping of electrodes in these manners may also introduce additional focusing power of the lens element under operation.

The polymer dispersed liquid crystal layer 1230 and 1235 may be located between the first transparent electrode 1220 and a second transparent electrode 1240. The second transparent electrode 1240 may be attached to the bottom substrate layer 1245, wherein the device formed from top substrate layer 1210 to the bottom substrate layer 1245 may comprise the variable optic portion of the ophthalmic lens.

Two alignment layers may also be located upon the dielectric layer and may surround the liquid crystal layer 1230 and 1235. The alignment layers may function to define a resting orientation of the ophthalmic lens. In some embodiments, the electrode layers 1220 and 1240 may be in electrical communication with liquid crystal layer 1230, 1235 and cause a shift in orientation from the resting orientation to at least one energized orientation.

In FIG. 12B, the effect of energizing of the electrode layers is depicted. The energizing may cause an electric field to be established across the device as illustrated at 1290. The electric field may induce the liquid crystal molecules to realign themselves with the formed electric field. As depicted at 1260 in the droplets containing liquid crystal, molecules may realign, as depicted by the now vertical lines.

Figures 13A, 13B, 13C:
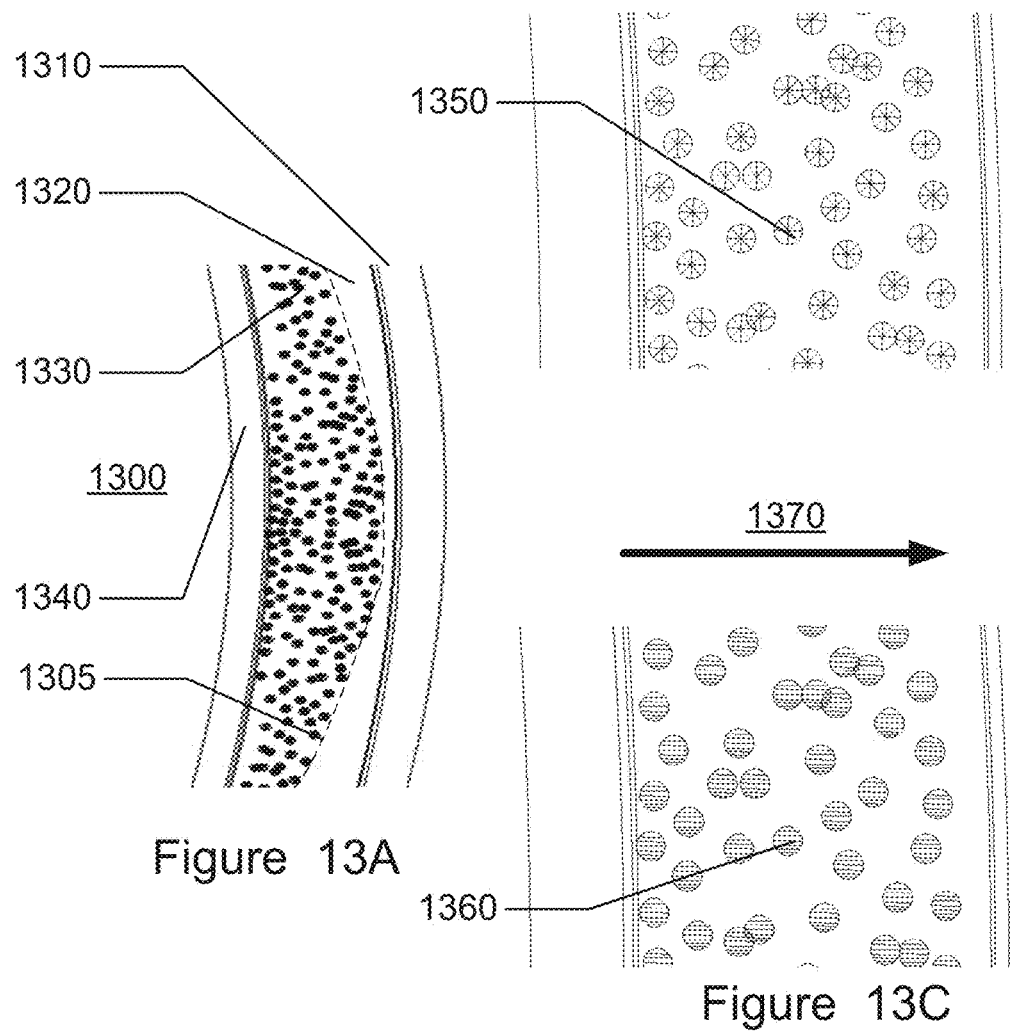
FIGS. 13A-C illustrate an alternative exemplary embodiment of a variable optic insert wherein the variable optic portion may be comprised of liquid crystal.

Referring to FIGS. 13A-C, an alternative of a variable optic insert 1300 that may be inserted into an ophthalmic lens is illustrated with a liquid crystal layer comprising polymerized regions 1320 and liquid crystal rich droplets 1330. Each of the aspects of the various elements that may be defined around the liquid crystal region may have similar diversity as described in relation to the variable optic insert in FIG. 12A-B. Therefore, there may be a front optic element 1310 and a back optic element 1340 where in some exemplary embodiments these optic elements may have one or more of electrodes, dielectric layers and alignment layers for example upon them. Referring to FIG. 13A, a global pattern in the location of droplets may be observed as may be illustrated by the dashed line 1305. The polymerized region around 1320 may be formed in such a manner as to be devoid or relatively devoid of droplets whereas droplets such as 1330 may form in other locations. A shaped profile of droplets, as illustrated by a border at 1305, may define additional means to form devices using a liquid crystal layer of a variable optic insert. Optical radiation that traverses the liquid crystal layer will have the accumulated effect of the droplet regions that it interacts with. Thus, portions of the layer that present a higher number of droplets to light will effectively have a higher effective index of refraction to the light. In an alternative interpretation, the thickness of the liquid crystal layer may effectively be considered to vary with the boundary 1305 being defined where there are fewer droplets. Referring to FIG. 13B, the droplets may be nanoscaled and in some exemplary embodiments may be formed in a layer with no external orienting aspects. As shown at 1350, the droplets may have a non-aligned and random state for liquid crystal molecules within. Proceeding to FIG. 13C, the application of an electric field 1370 by the application of an electropotential to electrodes on either side of the liquid crystal layer may result in alignment of the liquid crystal molecules within the droplets as illustrated in the example of item 1360. This alignment will result in a change of the effective index of refraction that a light beam in the vicinity of a droplet will perceive. This coupled with the variation in the density or presence of droplet regions in the liquid crystal layer may form an electrically variable focusing effect by the change of effective index of refraction in an appropriately shaped region containing droplets with liquid crystal molecules. Although the exemplary embodiments with shaped regions of droplets have been illustrated with nano-sized droplets comprising the liquid crystal layers, there may be additional embodiments that result when the droplets are larger in sized and still further exemplary embodiments may derive from the use of alignment layers in the presence of larger droplet regions.

Figure 14A:
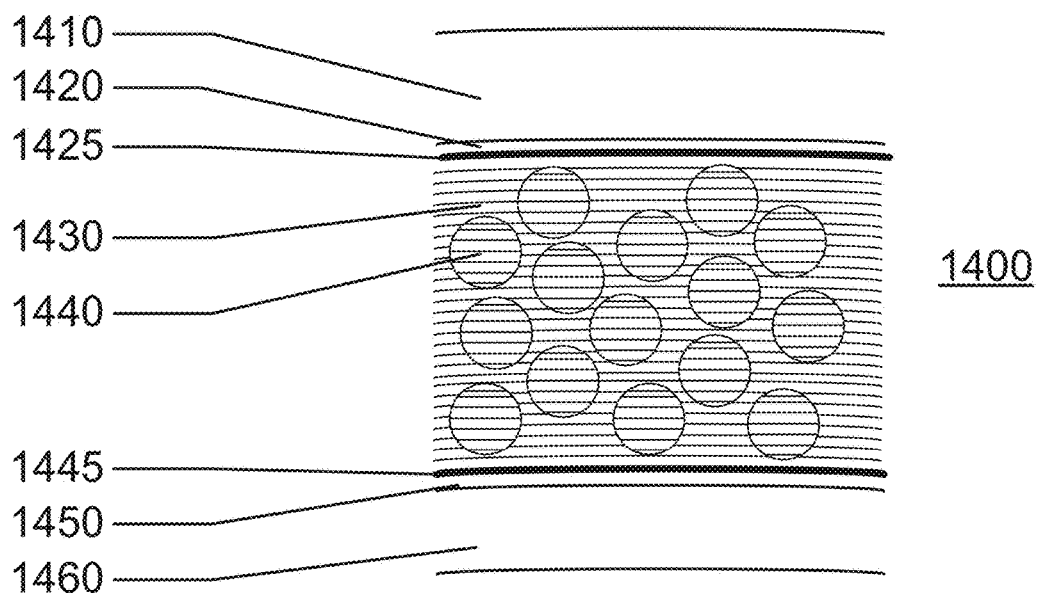
FIGS. 14A-B illustrate an alternative exemplary embodiment of a variable optic insert wherein the variable optic portion may be comprised of liquid crystal.

Liquid Crystal Devices Comprising Liquid Crystal Polymer Dispersed Liquid Crystal Layers Referring to FIG. 14A, a variable optic portion that may be inserted into an ophthalmic lens is illustrated with a liquid crystal polymer layer 1430 and a polymer dispersed liquid crystal layer 1440. A liquid crystal polymer dispersed liquid crystal layer may be comprised of isolated droplets, rich in liquid crystal molecules 1440 within other polymerized regions 1430. The polymerized regions may give the film structural definition and shape while the droplets rich in liquid crystal material may have a significant optical effect on light transmitting through the layer.

In applications where the refractive index effects of the liquid crystal layer are useful in creating a variable optic component, it may be useful to process the polymerized regions such that a significant amount of incorporated liquid crystal molecule is included within the gelled or polymerized regions. This incorporation may allow for the transmission of orienting effects from alignment layers incorporated in the surfaces of the insert device to the liquid crystal components within the polymer dispersed droplets, in the illustration of FIG. 14A incorporation of aligned liquid crystal molecules in both the polymerized regions and the droplets is depicted by the presence of the parallel lines across these regions. In addition, the liquid crystal molecules incorporated within the polymerized or gelled materials may allow for a relative matching of the refractive index of the polymer regions with the droplet regions both in resting states as well as when within an electric field. The relative matching of refractive index between the two components of the liquid crystal layer may minimize the scattering of light at interfaces between the regions.

There may be numerous manners to form a liquid crystal polymer dispersed liquid crystal layer of the type illustrated at FIG. 14A. In a first example, a mixture of a monomer and a liquid crystal molecule may be formed with the combination being heated to form a homogenous mixture. Next, the mixture may be applied to a front curve insert piece 1410 and then encapsulated in the lens insert by the addition of a back curve or intermediate insert piece 1460. The insert comprising the liquid crystal mixture may then be cooled at a controlled and predetermined rate. As the mixture cools, regions of relatively pure liquid crystal monomer may precipitate as droplets or droplets within the layer. A subsequent processing step to initiate polymerization of the monomer may then be performed. In some examples, actinic radiation may be directed to the mixture to initiate polymerization.

In another example, a mixture of liquid crystal and liquid crystal monomer may also be formed. In this example, the mixture may be applied to a front curve piece 1410 or a rear or intermediate curve piece 1460 and then the additional curved piece may be applied. The applied mixture may already include components to catalyze the polymerization reactions. Or, actinic radiation may be directed upon the mixture to initiate polymerization. With certain material choices for the monomer and catalyzing agents, the polymerization reaction may proceed at a rate and in such a manner that high concentration regions of liquid crystal monomer that are similar to droplets or droplets within the polymerized network of material. These droplets may be surrounded by polymerized material that also include an amount of liquid crystal molecules. These liquid crystal molecules may be free to move within the polymer matrix until it reaches a particular state of polymerization. The liquid crystal molecules may also be able to feel orienting effects in their neighboring regions which may be other liquid crystal molecules or alignment features on the surfaces of the insert pieces that the liquid crystal mixture was applied to. The alignment regions may determine a resting state for the liquid crystal molecules within the polymer matrix. As well, the aligned liquid crystal molecules in the polymer may also exert an orienting effect on the liquid crystal molecules within droplets or droplets of liquid crystal molecules. Thus, the layer of combined polymerized regions and included droplet regions may exist in a natural alignment state predetermined by the inclusion of alignment features upon the insert pieces before the insert is formed with the liquid crystal intermediate layer.

There may be numerous manners to incorporate liquid crystal molecules into the polymerized or gelled regions. In the previous descriptions some manners have been described. Nevertheless, any method of creating polymer dispersed liquid crystal layers may comprise art within the scope of the present invention and may be used to create an ophthalmic device. The previous examples mentioned the use of monomers to create polymerized layers that surround droplets of liquid crystal molecules. The state of the polymerized monomers may be a crystalline form of polymerized material, or in other embodiments may also exist as a gelled form of polymerized monomer.

The variable optic portion at FIG. 14A may have other aspects that may be defined by a similar diversity of materials and structural relevance as has been discussed in other sections of this specification. In some exemplary embodiments, a transparent electrode 1450 may be placed on the first transparent substrate 1460. The first lens surface 1445 may be comprised of a dielectric film, and in some exemplary embodiments, alignment layers which may be placed upon the first transparent electrode 1450. In such exemplary embodiments, the shape of the dielectric layer of the first lens surface 1445 may form a regionally varied shape in the dielectric thickness as depicted. Such a regionally varied shape may introduce additional focusing power of the lens element above the geometric effects discussed in reference to FIG. 3. In some exemplary embodiments, for example, the shaped layer may be formed by injection molding upon the first transparent electrode 1445 substrate 1450 combination.

In some exemplary embodiments the first transparent electrode 1445 and the second transparent electrode 1425 may be shaped in various manners. In some examples, the shaping may result in separate distinct regions being formed that may have energization applied separately. In other examples, the electrodes may be formed into patterns such as a helix from the center of the lens to the periphery which may apply a variable electric field across the liquid crystal layer 1430 and 1440. In either case, such electrode shaping may be performed in addition to the shaping of dielectric layer upon the electrode or instead of such shaping. The shaping of electrodes in these manners may also introduce additional focusing power of the lens element under operation.

The polymer dispersed liquid crystal layer 1430 and 1440 may be located between the first transparent electrode 1450 and a second transparent electrode 1420. The second transparent electrode 1420 may be attached to the top substrate layer 1410, wherein the device formed from top substrate layer 1410 to the bottom substrate layer 1450 may comprise n the variable optic portion 1400 of the ophthalmic lens. Two alignment layers may also be located at 1445 and 1425 upon the dielectric layer and may surround the liquid crystal layer 1430 and 1440. The alignment layers at 1445 and 1425 may function to define a resting orientation of the ophthalmic lens. In some embodiments, the electrode layers 1420 and 1450 may be in electrical communication with liquid crystal layer 1430, 1440 and cause a shift in orientation from the resting orientation to at least one energized orientation.

Figure 14B:
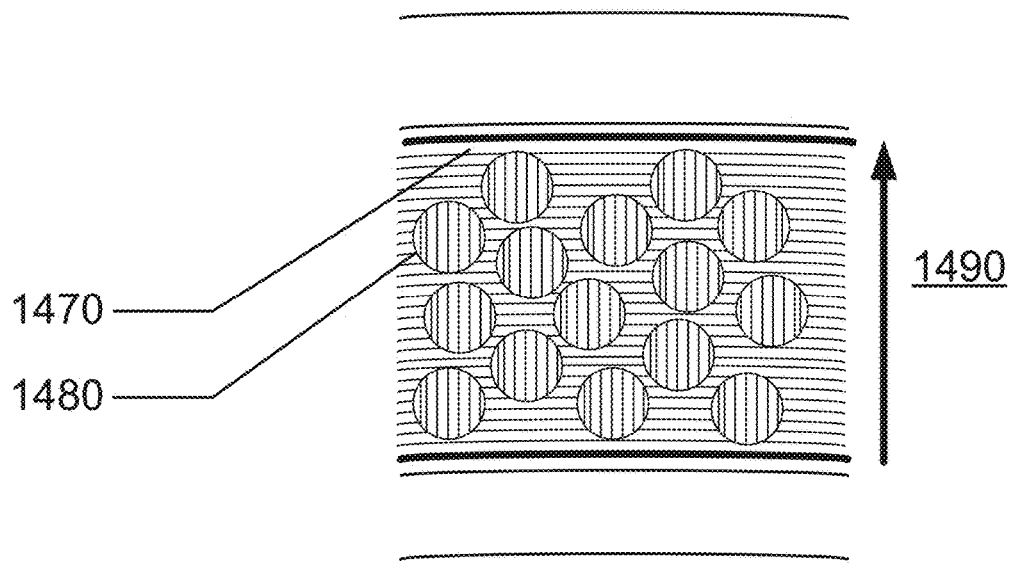

In FIG. 14B, the effect of energization of the electrode layers is depicted. The energization may cause an electric field to be established across the device as illustrated at 1490. The electric field may induce the liquid crystal molecules to realign themselves with the formed electric field. As depicted at 1470 for molecules in the polymerized portions of the layer and at 1480 in the droplets containing liquid crystal, molecules may realign, as depicted by the now vertical lines.

Figure 15:
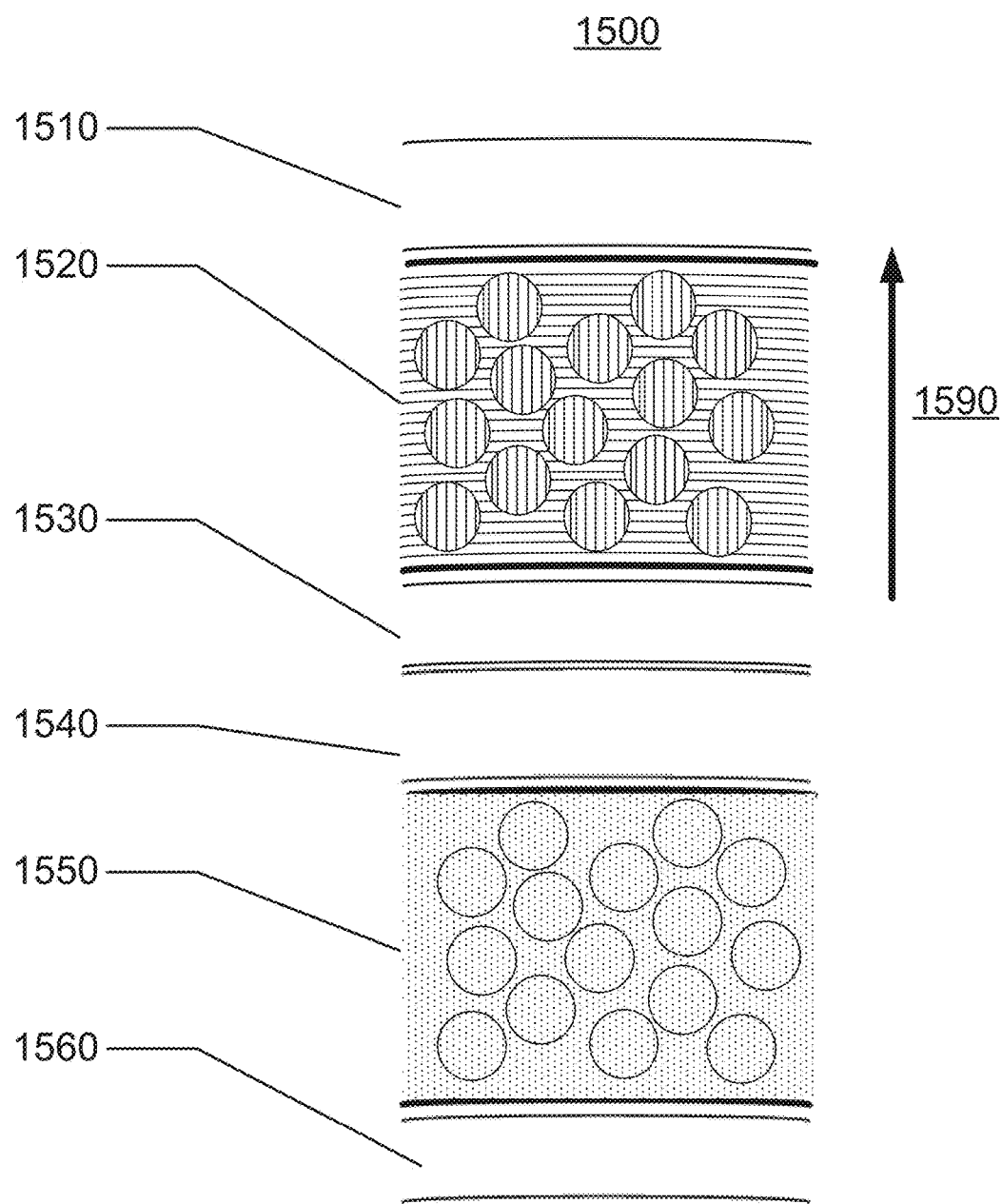
FIG. 15 illustrates an alternative exemplary embodiment of a variable optic insert wherein the variable optic portion may be comprised of liquid crystal.

Referring to FIG. 15, an alternative of a variable optic insert 1500 that may be inserted into an ophthalmic lens is illustrated with two liquid crystal layers 1520 and 1550 each of which may be liquid crystal and polymer dispersed liquid crystal layers as discussed in reference to FIGS. 14A and 14B. Each of the aspects of the various layers around the liquid crystal region may have similar diversity as described in relation to the variable optic insert in FIG. 14A and FIG. 14B. In some exemplary embodiments, the alignment layers may introduce polarization sensitivity into the function of a single liquid crystal element. By combining a first liquid crystal based element formed by a first substrate 1510, the intervening layers in the space around 1520 and a second substrate 1530 with a first polarization preference, with a second liquid crystal based element formed by a second surface on the second substrate 1540, the intervening layers in the space around 1550 and a third substrate 1560 with a second polarization preference, a combination may be formed which may allow for an electrically variable focal characteristic of a lens that is not sensitive to the polarization aspects of incident light upon it. The dot features in the illustration of region 1550 may depict aligned liquid crystal molecules whose alignment is perpendicular to the alignment of aligned molecules in the layer at 1520. An applied electric field at 1590 illustrates that an electrical field across either of the two liquid crystal layers may induce a realignment of the liquid crystal molecules in the droplet regions. In some exemplary embodiments, there may be separate ability to apply electric fields across either of the liquid crystal regions 1520 and 1550, as is depicted in FIG. 15. In other exemplary embodiments the application of an electric potential to the electrodes of the ophthalmic device may simultaneously energize both layers.

At the exemplary element 1500, a combination of two electrically active liquid crystal layers of the various types and diversity associated with the example in FIGS. 14A and 14B may be formed utilizing four substrate layers 1510, 1530, 1540 and 1560. In other examples, the device may be formed by the combination of three different substrates where the intermediate substrate may result from a combination of the 1530 and 1540 pieces shown. The use of four substrate pieces may present a convenient example for the manufacturing of the element where similar devices may be constructed around both the 1520 and 1550 liquid crystal layers where the processing difference may relate to the portion of steps that define alignment features for the liquid crystal element. In still further examples, if the lens element around a single liquid crystal layer such that depicted in FIG. 14A at 1400 is spherically symmetric or symmetric upon a rotation of ninety degrees, then two pieces may be assembled into a structure with the four substrate piece of the type depicted at 1500 by rotating the two individual insert pieces each made from two substrate pieces ninety degrees relative to each other before assembling.

Figures 16A, 16B:
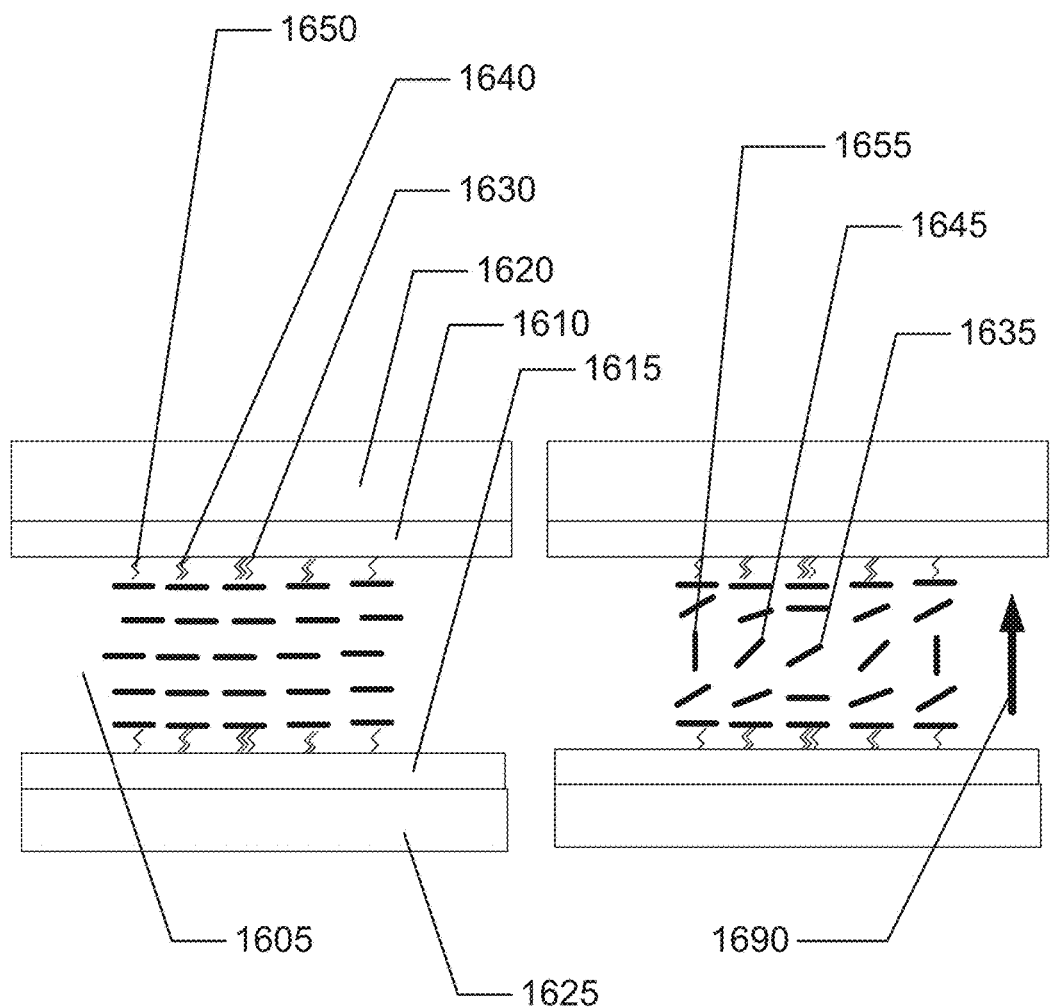
FIGS. 16A-B illustrate an alternative exemplary embodiment of a variable optic insert wherein the variable optic portion may be comprised of liquid crystal.

Ophthalmic Devices Comprising Liquid Crystal Layers with Varied Anchoring Strength Referring to FIG. 16A, an exemplary depiction of an ophthalmic device comprising liquid crystal layers comprising varied anchoring strength may be found. An ophthalmic insert may be comprised of a front curve piece 1620 and a back curve piece 1625 upon which have been placed a front curve electrode layer 1610 and a rear curve electrode layer 1615. In some exemplary embodiments, an anchoring layer of material may be added upon the surface of the electrode layers or in some cases upon a dielectric layer that is upon the electrode layers. The surface of the anchoring layer may be modified in various chemical or physical manners such that the surface interaction with subsequently applied liquid crystal layers 1605 may vary spatially across the treated surface. In an illustrative manner where the scale and physical phenomena are not depicted at the actual scale, the anchoring strength may be depicted at 1630, 1640 and 1650. If the bond strength of the anchoring location at 1630 is enhanced, denoted by the three anchoring bonds, then the effect of that anchoring of liquid crystal molecules upon the surface region may be communicated to neighboring liquid crystal molecules throughout the layer. The bond strength of the surface region 1640, illustrated by two anchoring bonds, may be less strong when compared to region 1630, but also may be stronger than the surface region at 1650, the anchoring strength of which is illustrated by a single anchoring bond. In a static and non-energized mode, the liquid crystals of the liquid crystal layer 1605 may align in a preferred fashion depicted by the rod shaped illustrations of liquid crystal molecules lying in a generally parallel fashion to the surface topography.

In the presence of an electric field, depicted at 1690, the liquid crystal molecules may interact with the electric field and have forces upon them to orient along the electric field that has been established. As mentioned previously, the strength of the anchoring interaction may be communicated through the liquid crystal layer and result in a different shift in orientation for liquid crystal molecules in different locations proximate to the surface anchoring sites. For example, the strongly interacting regions may have liquid crystal molecules that lay nearly unperturbed at 1635 by the electric field 1690. Whereas, the most weakly anchored regions may completely align at 1655 with the electric field 1690. In addition, as depicted at 1645, the orientation may assume intermediate states of alignment with the electric filed 1690 at regions of intermediate anchoring strength 1640.

Therefore, a spatially uniform orientation of molecules such as the molecules in FIG. 16A may assume a regionally variable orientation in the presence of an electric field as depicted in FIG. 16B. Since the liquid crystal molecules may present a different index of refraction to incident radiation based on its alignment relative to the incident radiation, the ability to control regionally varying orientations based on the treatment of an anchoring layer may allow for a programmed optical effect to be activated when the electrodes 1615 and 1625 are energized to create an electric field 1690. As well, the details of the variation of index of refraction in a spatial sense may also be smoothly varied based on the strength of the electric field that is applied. This may in turn be controlled by a level of electric field potential or voltage that is applied across the electrode layers. Therefore, optical devices comprising liquid crystal layers applied to anchoring layers that have regionally defined and varying strength of anchoring interaction with the liquid crystal layers may result in devices with a bistable characteristic of a spatially altered index of refraction profile in an energized state versus a nonenergized state, or alternatively, there may be a continuum of optical characteristics resulting from energization of the electrodes to varied electro-potentials or voltages.

Ophthalmic Devices Comprising Liquid Crystal Layers with Varied Anchoring Direction (Pretilt)

Figure 17A:
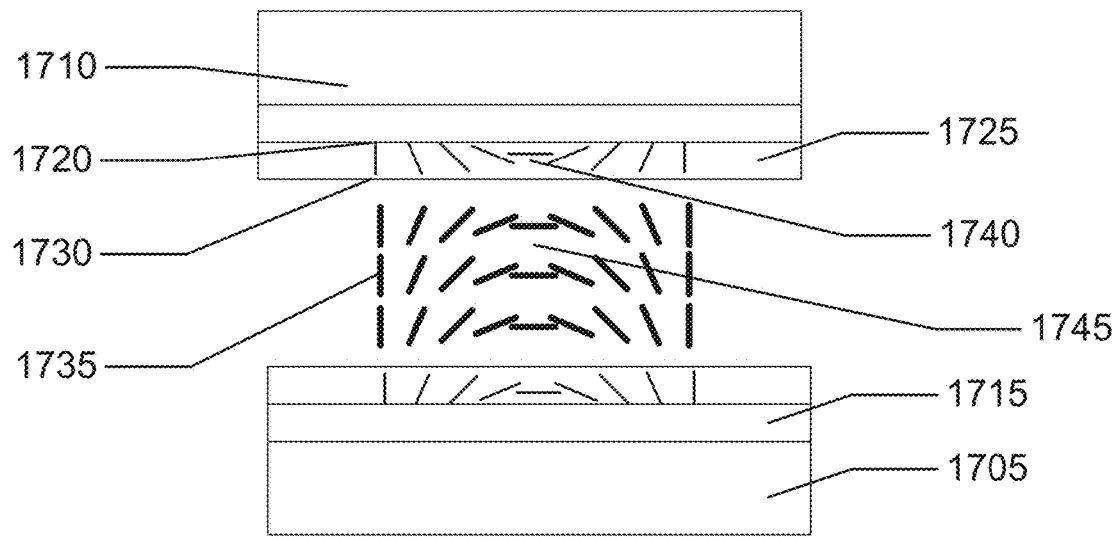
FIGS. 17A-B illustrate an alternative exemplary embodiment of a variable optic insert wherein the variable optic portion may be comprised of liquid crystal.
Figure 17B:
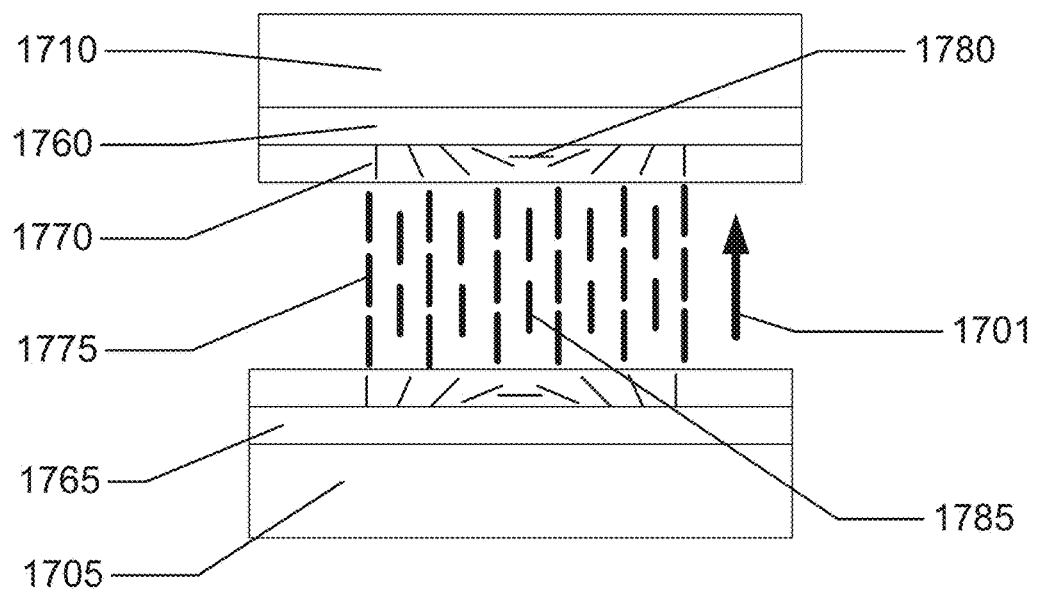

Referring to FIGS. 17A-B a similar but alternate exemplary embodiment to design spatial variation in the alignment of liquid crystal layers in between electrode regions may be found. At FIG. 17A, an exemplary depiction of an ophthalmic device comprising liquid crystal layers comprising varied alignment orientation may be found. An ophthalmic insert may be comprised of a front curve piece 1705 and a back curve piece 1710 upon which have been placed a front curve electrode layer 1715 and a rear curve electrode layer 1720. In some exemplary embodiments, a layer of material capable of aligning molecules in their vicinity in liquid crystal layers may be added upon the surface of the electrode layers or in some cases upon a dielectric layer that is upon the electrode layers. The aligning layer 1725 may be formed or treated after formation in such a manner by various chemical or physical treatments such that the layer forms with its molecules oriented in a variable but programed manner across its surface. Some of these orientations may induce liquid crystal molecules to align in a first orientation as depicted at 1735 in the vicinity of the alignment layer at 1730 to an orientation that may be fully perpendicular to the first alignment orientation 1735 which may be depicted at 1745 for molecules in the vicinity of the alignment layer at 1740.

The discussion has focused on the orientation of molecules in the aligning layer at a first surface, but in fact in an ophthalmic insert with a front curve and a back curve, the processing of the alignment layer may be conducted upon each of the surfaces. In some exemplary processing the spatially varying pattern on the front curve piece may have an equivalently defined spatial pattern on the back curve piece. In these cases, the orientation of molecules within the liquid crystal layer may be illustrated to be uniform across the layer while the orientation may vary in space along the surface pieces as depicted in FIG. 17A. In other exemplary embodiments, a different spatial pattern may be formed in the alignment layer upon the front curve piece when compared to the spatial pattern formed upon the alignment layer upon the back curve piece of the ophthalmic insert device. Such an embodiment may result in controlled by varying alignment of liquid crystal molecules across the surfaces of ophthalmic insert devices, as well as the additional variation of alignment in a controlled fashion at a given spatial location of the surface of the orientation from a front optic piece across the liquid crystal layer to a back optic piece.

Referring to FIG. 17B, a depiction of the effect of an applied electric field upon the orientation of molecules in the liquid crystal layer is depicted. At 1701 an electric field is established by the application of an electrical potential to the two electrodes 1760 and 1765, which are respectively located upon the front curve piece 1710 and the back curve insert piece 1705. It may be observed that the orientation of molecules of the alignment layers illustrated by 1770 and 1780 may not be altered in the exemplary depiction by the application of an electric field 1701. Nevertheless, the interaction of the electric field with the liquid crystal molecules may be such that it may dominate the interaction of the alignment layers, and molecules in the liquid crystal layer may therefore align with the electric filed as depicted by items 1775 and 1785. It may be noted, that the illustration may represent a simplification of the actual situation since in the regions very close to the alignment layers, there may be orientations that are not as aligned as may be illustrated, yet the effect of the collection of liquid crystal molecules as a whole may be estimated as similar to that depicted with a relatively uniform alignment of the molecules across spatial locations and with the electric field.

There may be numerous manners to form the alignment layers depicted in an exemplary fashion at 1725 or for that matter any of the alignment layers referred to in the various embodiments herein. In one example, a dye material comprising molecules based upon the chemical backbone of azobenzene may be coated upon the electrode layer or upon a dielectric upon the electrode layer to itself form a layer. An azobenzene based chemical moiety may exist in a trans configuration and a cis configuration. In many examples, the trans configuration may be the more thermodynamically stable state of the two configurations and therefore at temperature around that of 30 Celsius, for example, most of the molecules of an azobenzene layer may be oriented in the trans state. Due to the electronic structure of the different molecular configurations the two configurations may absorb light at different wavelengths. Therefore, by irradiating, in an exemplary sense, with light at wavelengths in the 300-400 nanometer regime, the trans form of the azobenzene molecule may be isomerized to the cis-form. The cis form may relatively rapidly return to a trans configuration, but the two transformations may result in physical movements of the molecule as the transformations occur. In the presence of polarized light, the absorption of light may be more or less likely depending on the orientation of the trans-azobenzene molecule relative to the polarization vector and incidence angle of the light used to irradiate it. The resulting effect of the radiation with a particular polarization and incidence angle may be to orient azobenzene molecules in reference to the incident polarization axis and incidence plane. Therefore, by irradiating the alignment layers of azobenzene molecules to appropriate wavelength and with predetermined and spatially varying polarization and incidence angle, a layer with spatial variation in the alignment of the azobenzene molecules may be formed. The azobenzene molecules in a static sense also interact with liquid crystal molecules in their environment, thus creating the different alignment of liquid crystal molecules depicted in FIG. 17A.

Figure 17C:
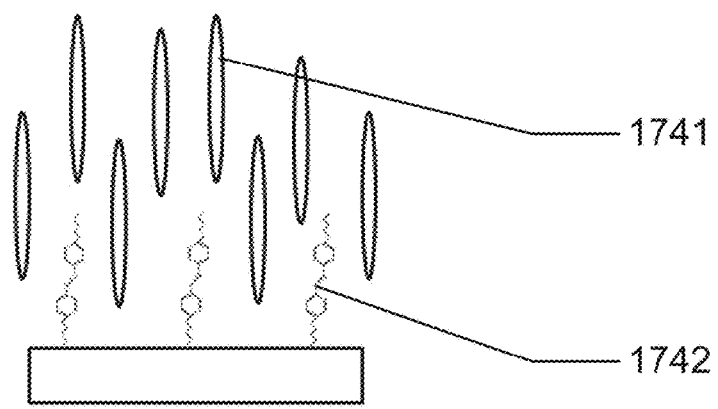
FIGS. 17C, D, E illustrate an alternative exemplary embodiment of an alignment layer for an exemplary embodiment of a variable optic insert wherein the variable optic portion may be comprised of liquid crystal.
Figure 17D:
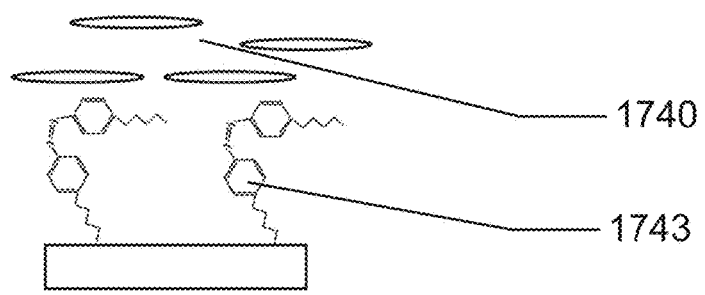
FIG. 17F illustrates an alternative exemplary embodiment of a variable optic insert wherein the variable optic portion may be comprised of liquid crystal and equations of merit for the type of embodiment.
Figure 17E:
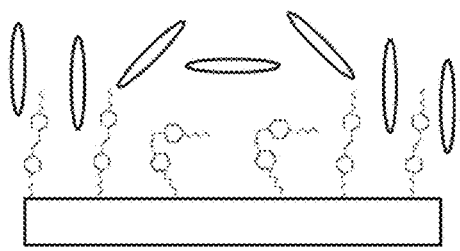

Azobenzene materials may also allow other opportunities for modulating the anchoring direction due to the opportunity of obtaining in-plane and out of plane orientation at trans and cis states as schematically shown in FIGS. 17C-E. These materials are sometimes referred to as command layers. Liquid crystal orientation modulation for such materials may also be obtained by spatially modulating actinic light intensity. Referring to FIG. 17C, azobenzene molecules at 1742 may be oriented in a trans configuration while also being anchored to the surface. In this configuration, liquid crystal molecules may orient as shown at 1741. In the alternative cis configuration azobenzene molecules 1743, may influence liquid crystal molecules to orient as shown at 1740. Referring to FIG. 17E, a combination of liquid crystal orientations is illustrated as may be consistent with the inventive concepts herein.

Other alignment layers may be formed in different manners, such as, the use of polarized incident radiation to control the spatial alignment of polymerized layers based upon preferred orientation of polymerization induced by the local polarized incident light.

Figure 17F:
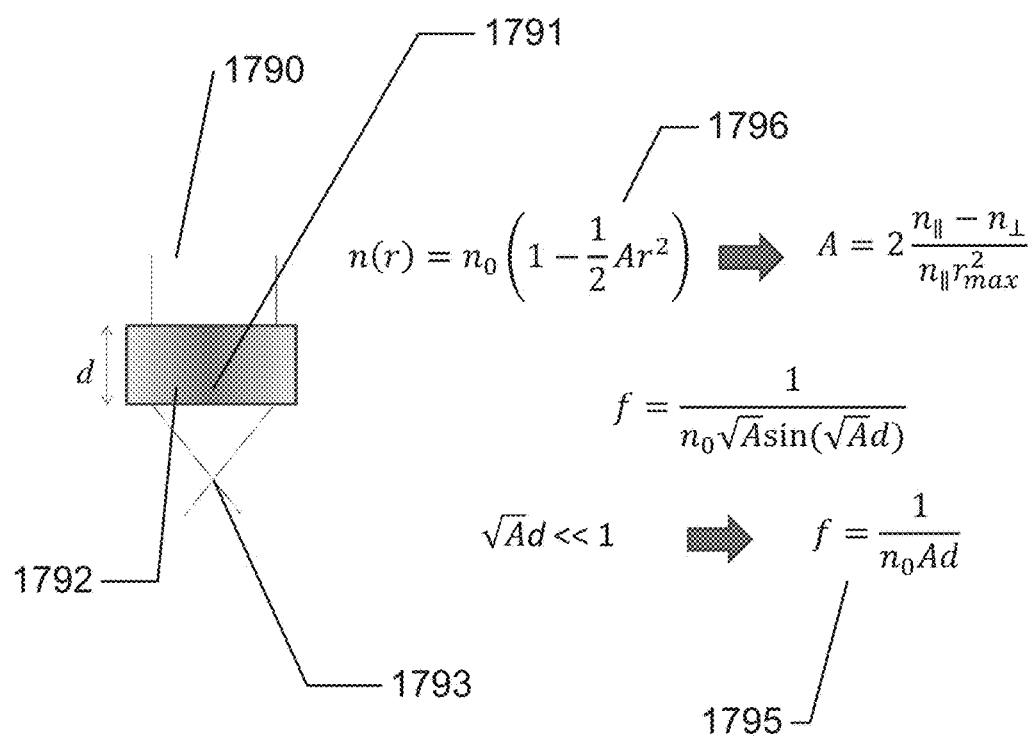

Referring to FIG. 17F, a representation of a gradient index optic is illustrated. The principles of anchoring depicted in reference to FIGS. 16A and B as well as the exemplary embodiments relating to alignment layers depicted in reference to FIGS. 17A, B and C may be used to create a parabolic variation of refractive index with radial distance, A relationship mathematically representing such a parabolic variation of index n(r) versus radial distance r may be found at 1796. A graphical representation of the phenomena for a flattened lens object may be found at 1790, where an index of refraction at 1791 may be a relatively high index which may be represented by a density of black color in the illustration. As the index varies radially such as depicted at 1792, the index may be a lower index of refraction as well as being depicted as a lessened density of black color. An optic may be formed with a parabolic variation of refractive index with radial distance and the effect on light may be shift in the phase of incident radiation to result in a focusing of light as depicted at 1793. A mathematic estimate of the focal characteristics of such a gradient indexed optic may be illustrated at 1795.

Ophthalmic Devices Comprising Cycloidal Waveplate Lens

Figure 18:
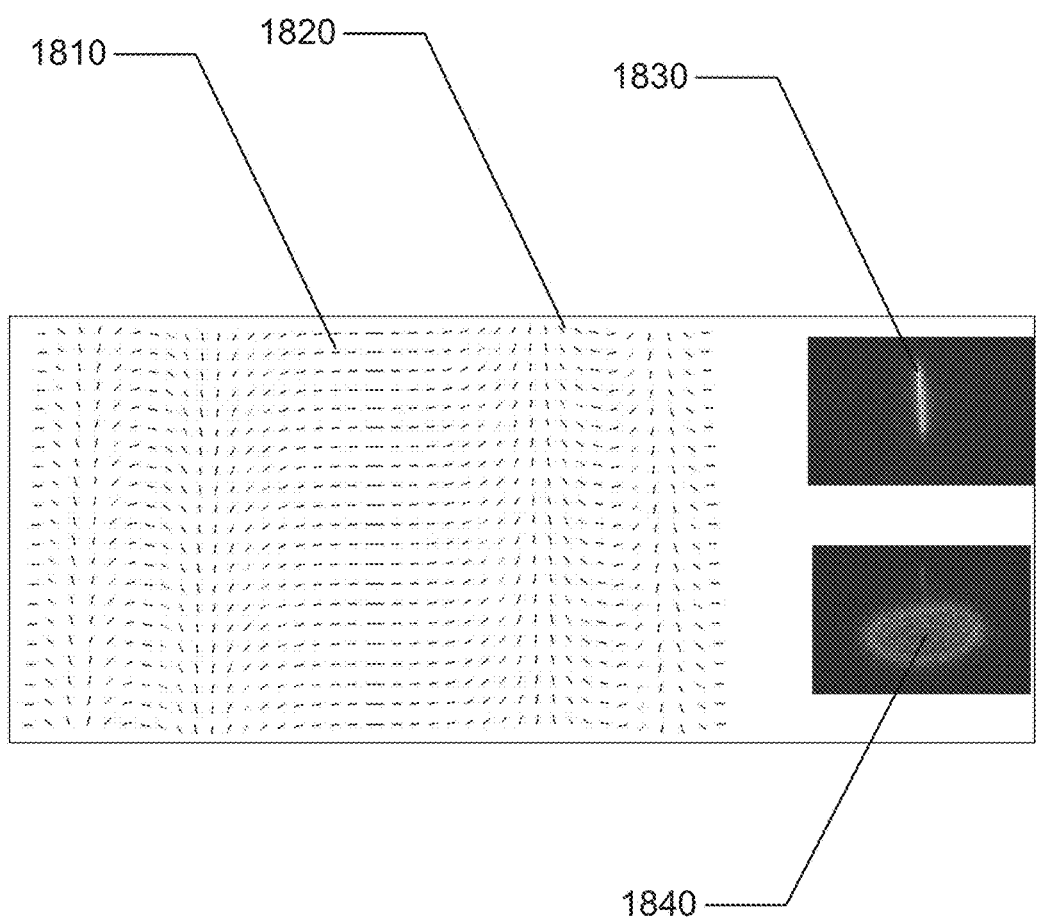
FIGS. 18 and 18A illustrates an exemplary embodiment of patterning of liquid crystals and exemplary optical results deriving from a device of said type.
Figure 18A:
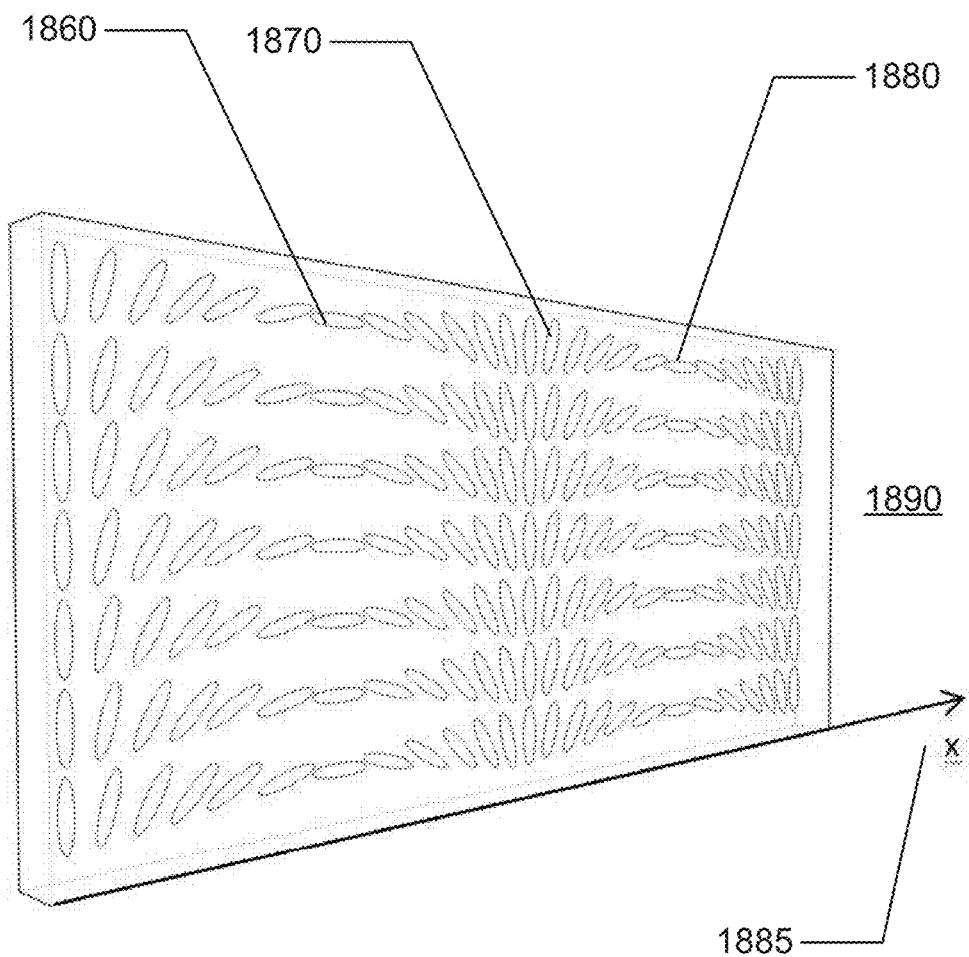

A special variety of polarization holograms; namely, cycloidal diffractive waveplates (CDW), provide substantially one hundred percent diffraction efficiency and may be spectrally broadband. The structure of cycloidal diffractive waveplates, schematically illustrated in FIG. 18, comprises anisotropic material film 1810, wherein the optical axis orientation is continuously rotating in the plane of the film as illustrated by the pattern 1820 in the film 1810. Typical optical results from such a waveplate may be found in reference to 1830 and 1840. Nearly one hundred percent efficiency for visible wavelengths is achieved at fulfillment of half-wave phase retardation condition typically met in approximately one micrometer (0.001 mm) thick liquid crystal polymer (LCP) films. Referring to FIG. 18A, a close up illustration of the orientation programing that may occur in a cycloidal waveplate design may be found at 1890. In a given axis direction, 1885 for example, the pattern may vary from orientation parallel to the axial direction 1860, through orientations towards a perpendicular orientation to the axial direction 1870 and again back through a parallel orientation to the axial direction at 1880.

Such an unusual situation in optics where a thin grating exhibits high efficiency, may be understood by considering a linearly polarized light beam of wavelength A incident normally, along the z-axis, on a birefringent film in the x,y plane. If the thickness of the film L and its optical anisotropy, $\Delta n$, are chosen such that $L\Delta n=\lambda/2$, and its optical axis is oriented at forty-five (45) degrees, angle $\alpha$, with respect to the polarization direction of the input beam, the polarization of the output beam is rotated by ninety (90) degrees, angle $\beta$. This is how half-wave waveplates function. The polarization rotation angle at the output of such a waveplate, $\beta=2\alpha$, depends on the orientation of the optical axis d=(dx, dy)=(cos $\alpha$, sin $\alpha$). Liquid crystal materials, both low molecular weight as well as polymeric, allow continuous rotation of d in the plane of the waveplate at high spatial frequencies, □=qx, where the spatial modulation period □=2□/q may be comparable to the wavelength of visible light. Polarization of light at the output of such a waveplate is consequently modulated in space, β=2qx, and the electric field in the rotating polarization pattern at the output of this waveplate is averaged out, <E>=0, and there is no light transmitted in the direction of the incident beam. The polarization pattern thus obtained corresponds to the overlap of two circularly polarized beams propagating at the angles ±□/□. Only one of the diffraction orders is present in the case of a circularly polarized input beam, the +1st or −1st, depending on whether the beam is right or left handed.

A special variety of cycloidal diffractive waveplates are illustrated at FIG. 19A. In such an exemplary embodiment, the cycloidal diffractive waveplate pattern referred to in FIG. 18 may be further refined in the form factor of ophthalmic lens insert devices. In the illustration, the shape has been portrayed in a flattened manner, but a similar orientation programming shape may occur across three dimensional surfaces such as lens inserts as well. At 1910, a cycloidal diffractive waveplate pattern may be spirally rotated into a radial pattern that may be located upon a flat surface or upon a folded surface such as a subtended portion of a spherical surface, and the rotation angle of liquid crystal or liquid crystal polymer molecules may be modulated in a parabolic function from the center of the waveplate. Such a structure acts like a lens with advantages compared to other liquid crystal lenses that may include that different or higher strength of the lens (measured as focal length or in diopters) may be obtained within the same thickness or thinner films. In some exemplary embodiments, the thickness of the film that may be only 1-5 □m. Another advantage of the lens may be the opportunity of switching between positive and negative values for focal power adjustment by the switching of the polarization of light incident upon the device. In some exemplary embodiments, the use of a liquid crystal phase retardation plate may be used to facilitate the polarization switching. Decoupling between the lensing action and switching action may allow versatility in electrical characteristics of the system, such as capacitance and power consumption, as non-limiting examples. For example, even if the lens itself may be chosen to be thin, the thickness of the liquid crystal phase retarder may be chosen to minimize power consumption.

A cycloidal diffractive lens pattern formed within the space between a front insert piece and a back insert piece may form an electrically active embedded variable optic insert. As shown in FIG. 19B by the application of electric potential to electrodes in the front and back insert pieces an electric field 1990 may be established across the cycloidally oriented liquid crystal layer. When liquid crystal moieties align with the electric field as depicted at 1920, the resulting alignment may render the liquid crystal layer to become a spatially uniform film without the special properties of a diffractive waveplate lens. Thus, as a non-limiting example, a pattern at 1910 that has an optical power may not cause a focusing effect with the application of an electric field as depicted at 1920.

Figure 20:
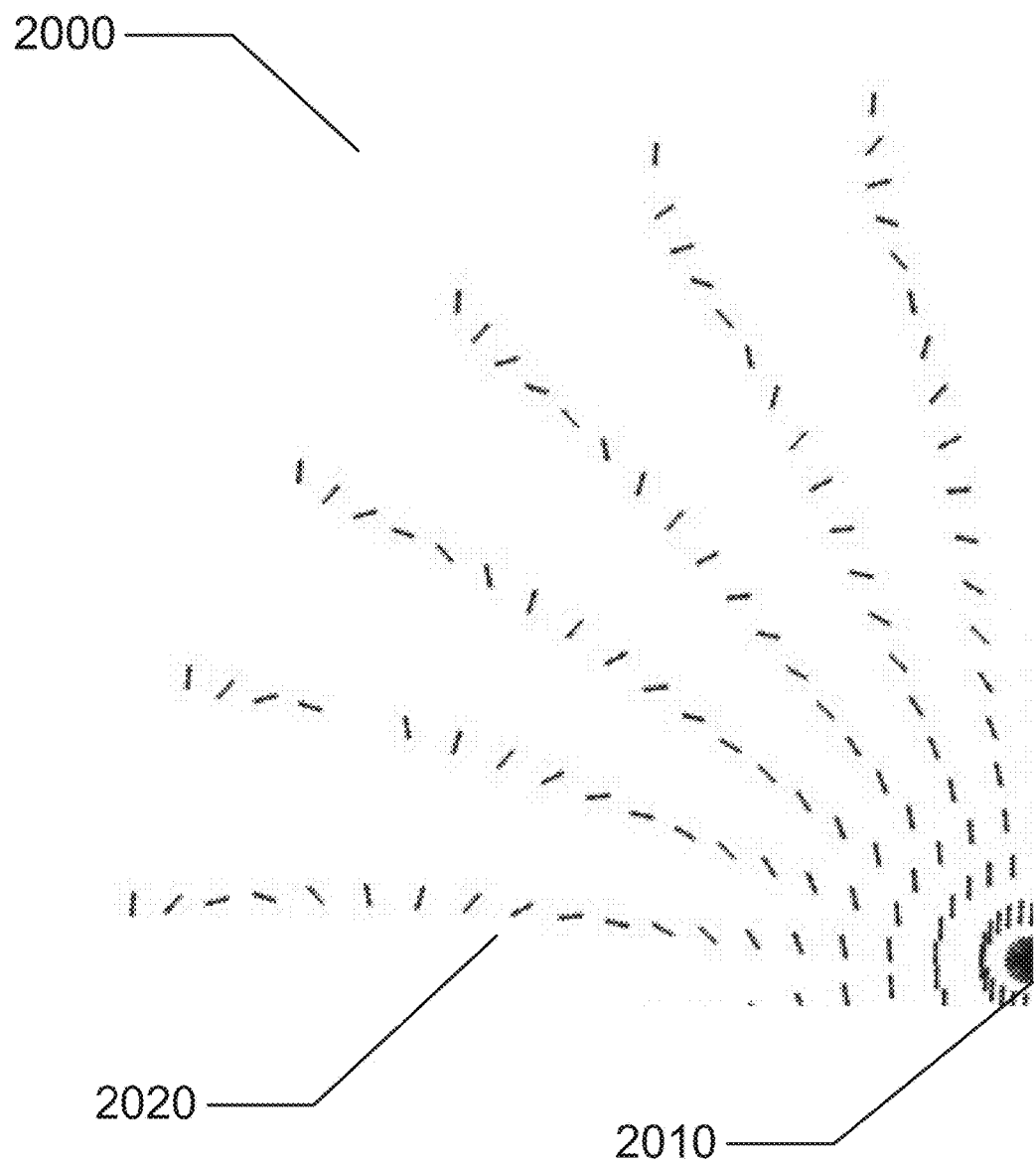
FIG. 20 illustrates a close-up of the embodiments of the type illustrated in FIG. 19.

A close up illustration of alignment of liquid crystal molecules for cycloidal waveplate type embodiments may be found referring to FIG. 20 item 2000. A quarter of the pattern is illustrated and the orientation shift of the alignment of molecules from the center of the lens 2010 radially outward as for example to 2020 and to the outside may be observed. It may be observed that the orientation may be similar to a radial rotation of the programming pattern illustrate in relationship to FIG. 18 for example.

Fabrication of liquid crystal and liquid crystal polymer diffractive waveplates may be a multistep process. The technology for printing cycloidal diffractive waveplates from a master waveplate may be fit for large-scale production with high quality and large areas. This may be compared to other embodiments involving holographic equipment which may add complexity, cost and stability problems. The printing technique may make use of the rotating polarization pattern obtained at the output of the master cycloidal diffractive waveplate from a linearly or circularly polarized input beam. The period of the printed waveplates may be doubled when one uses a linearly polarized input beam. As compared to direct recording in photoanisotropic materials, liquid crystal polymer technology based on photoalignment may have an advantage based upon the commercial availability of liquid crystal polymers, for example, from Merck. A typical liquid crystal polymer of reactive mesogens which may be referenced in a supplier's (Merck) nomenclature, such as RMS-001C, may be spin coated (typically three thousand (3000) rpm for sixty (60) s) on a photoalignment layer and UV polymerized for approximately ten (10) minutes. Multiple layers may be coated for broadband diffraction or for adjusting the peak diffraction wavelength.

Ophthalmic Devices Comprising Shaped Dielectric Layers with Polymer Dispersed Liquid Crystal Layers Referring to FIG. 21, an exemplary embodiment of an ophthalmic device comprising shaped dielectric layers may be found. The exemplary embodiment shares numerous aspects discussed in relationship to the exemplary embodiments related to FIG. 10. At 2140 a shaped dielectric layer corresponding to the similar feature at 1040 may be found. In exemplary embodiments relating to FIG. 21, the dielectric layer 2140 may be formed through controlled polymerization of the monomer moiety used to form polymer dispersed liquid crystal layers. In some exemplary embodiments, the layer 2140 may comprise amounts of liquid crystal molecules entrapped during the polymerization processes. If the surface upon which the layer 2140 is formed has an alignment layer such as 2170, the liquid crystal molecules may be aligned to the patterns of the alignment layer and be aligned while the polymerized layer 2140 is formed in some exemplary embodiments.

The processing of the monomer comprising liquid crystal molecules may subsequently be polymerized under such conditions that polymer dispersed voids, such as 2130 may be formed comprising liquid crystal molecules. In other regions of the subsequently polymerized layer at 2120, the polymer layer comprising liquid molecules may be formed. In some exemplary embodiments there may be an alignment layer at 2165 which may also orient liquid crystal molecules during the polymerization process.

The illustration of FIG. 21 depicts an exemplary embodiment where there are front 2110 and back 2150 substrates between which the electrode layers 2160 and 2175 as well as alignment layers 2170 and 2165 may be located. The alignment layers may be formed and patterned in manners described previously or may be performed by industry standard rubbing processes, for example. The depiction of FIG. 21 illustrates a flat orientation of the various layers. This depiction is for exemplary purposes alone and curved optic pieces such as may be located in ophthalmic devices such as contact lenses may share the structural order if not the shape as depicted. In some exemplary embodiments, such as those where the void features 2130 are nanoscaled there may not be the need for alignment layers in the structure. In these features the random orientation of the molecules in the void layers may be desirable.

In addition, as described previously in reference to polymer dispersed liquid crystal layers formed within ophthalmic insert devices, the creation of an electric field through the liquid crystal layers by the application of electro-potential across the electrode layers may cause the liquid crystal layers which are present in the voids to align with the electric field and shift the index of refraction presented to light that traverses the ophthalmic device. The shaped dielectric, 2140 may cause the local electric field through any part of the liquid crystal layer to vary with the shaped dielectric profile. In some exemplary embodiments, the shaped dielectric layer may be formed of a material with a similar optical dielectric characteristic compared to the polymer dispersed liquid crystal layer but a different electrical dielectric characteristic.

Referring to FIGS. 21A and 21B, individual droplets 2131 of liquid crystal are illustrated to demonstrate the various orientation aspects that may be possible. In some exemplary embodiments, especially where the droplets are of a nanoscaled size, the non-energized orientation at FIG. 21A may have droplets where the liquid crystal molecules exhibit a random orientation pattern as shown. In other exemplary embodiments, the use of alignment layers may create a non-energized orientation configuration where for example the molecules may be aligned parallel to a surface such as shown in FIG. 21B at 2132. In either of these cases when an electric field is applied, 2190, the liquid crystal molecules may align with the electric field as demonstrated in FIG. 21C at 2133.

Ophthalmic Devices Comprising Polymer Dispersed Liquid Crystal Layers with Varied Density of Liquid Crystal Droplets in the Polymer Layer Referring to FIG. 22, another exemplary embodiment of an ophthalmic device comprising liquid crystal layers may be found. In exemplary embodiments that share similarity to exemplary embodiments related to FIG. 13A, a liquid crystal layer may be formed for optical effects where the density of liquid crystal droplets in the polymer layer is varied across the radial layer in a transverse sense. As depicted in FIG. 22, item 2210 and item 2260 may represent front insert and back insert pieces respectively. Upon these pieces may be layers or combinations of layers represented by 2250 and 2220. The layers 2250 and 2220 may represent electrode layers that may also comprise dielectric layers and/or alignment layers thereupon. Between these layers, may be a layer 2240 comprising liquid crystal moieties. The layer 2240 may be processed in such a manner that regions of polymerized material may be interrupted by droplets containing primarily liquid crystal molecules such as at 2230. The depiction of FIG. 22 illustrates a flat orientation of the various layers. This depiction is for exemplary purposes alone and curved optic pieces such as may be located in ophthalmic devices such as contact lenses may share the structural order if not the shape as depicted. In some exemplary embodiments, such as those where the droplet features 2230 are nanoscaled there may not be the need for alignment layers in the structure. In these features the random orientation of the molecules in the void layers may be desirable.

By controlling the polymerization processing, the spatial control may be performed in such a manner that at a particular location of the liquid crystal comprising layer 2240, there may be a different density or amount of liquid crystal material from the front curve insert to the back curve region than at another location. These changes in the amount of liquid crystal material across the lens surface may be useful to program the aggregate index of refraction that light traversing the ophthalmic device would see at a particular region. Optical effects such as spherical focusing and higher order optical effects may be caused to occur. As in previous embodiments, the establishment of an electric field across the layer 2240 may result in the alteration in alignment of liquid crystal moieties which may result in the establishment of an altered optical effect of the ophthalmic device in an electroactive manner.

Referring to FIGS. 22A and 22B, individual droplets 2231 of liquid crystal are illustrated to demonstrate the various orientation aspects that may be possible. In some exemplary embodiments, especially where the droplets are of a nanoscaled size, the non-energized orientation at FIG. 22A may have droplets where the liquid crystal molecules exhibit a random orientation pattern as shown. In other exemplary embodiments, the use of alignment layers may create a non-energized orientation configuration where for example the molecules may be aligned parallel to a surface such as shown in FIG. 22B at 2232. In either of these cases when an electric field is applied, 2290, the liquid crystal molecules may align with the electric field as demonstrated in FIG. 22C at 2233.

Figure 23:
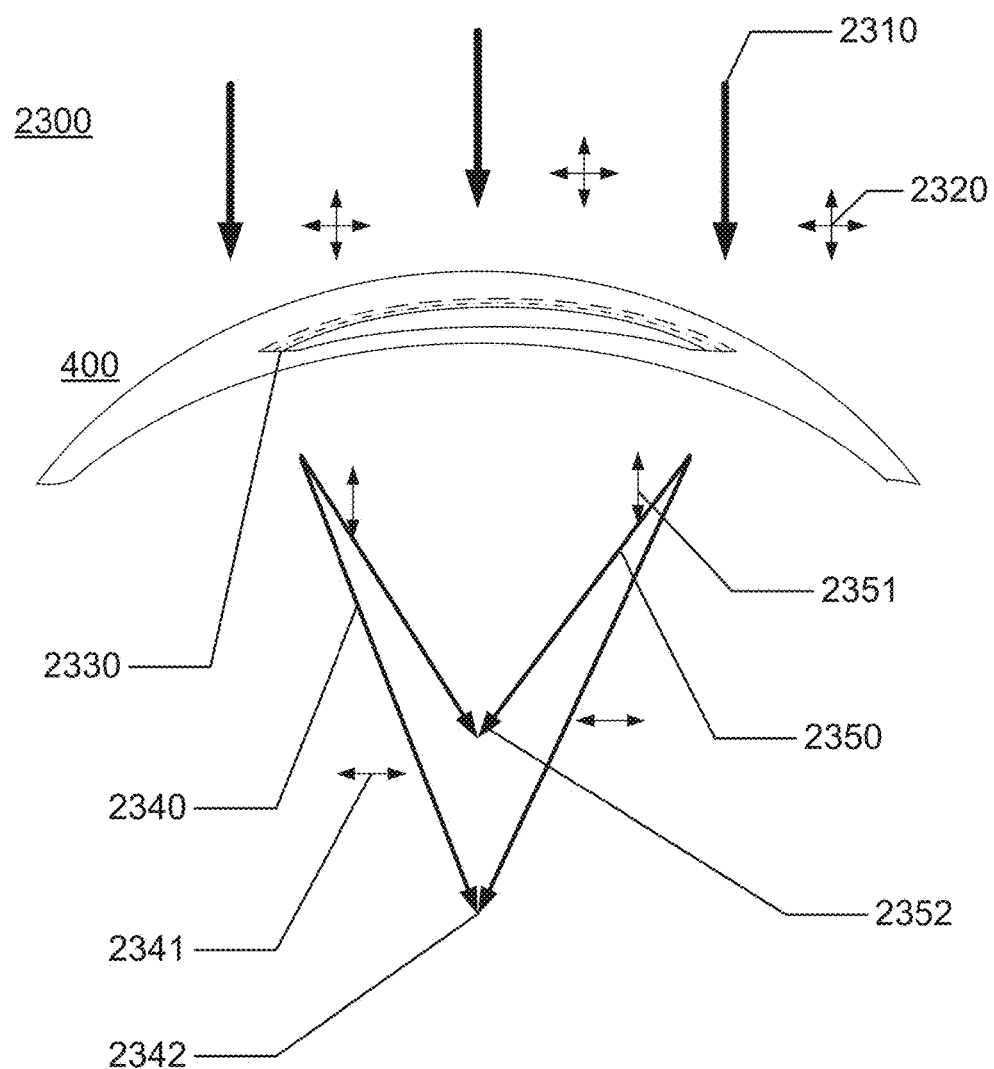
FIG. 23 illustrates an alternative exemplary embodiment of a variable optic insert wherein the variable optic portion may be comprised of liquid crystal and the manner that polarized light components may be affected while traversing the embodiment.

Bifocal Ophthalmic Devices Comprising Single Polarization Sensitive Liquid Crystal Layers with Active and Passive Aspects Referring to FIG. 23, a class of devices utilizing some of the various exemplary embodiments described may be found for bifocal ophthalmic devices comprising single polarization sensitive liquid crystal layers. An ophthalmic lens of the type described in FIG. 4 may be provided with an insert 2330 comprising a liquid crystal layer. The layer of the various types that have been described may be aligned by alignment layers and therefore have a sensitivity to a particular polarization state. If the device has a focal adjusting function and has a single aligned liquid crystal layer, or alternatively is a dual layer device, where one liquid crystal layer is aligned in an orthogonal direction to the other liquid crystal layer, and one of the liquid crystal layers is electrically energized to a different level than the other, then the light 2310 incident upon the ophthalmic lens 400 may be resolved into two different focal characteristics for each of the polarization directions. As depicted, one of the polarization components 2351 may be focused on a path 2350 towards a focal point 2352 whereas the other polarization component 2341 may be focused on a path 2340 towards focal point 2342.

In state of the art ophthalmic devices there are a class of bifocal devices that simultaneously present multiple focused images to a user's eye. A human's brain has a capability of sorting out the two images and seeing the different images. The device at 2300 may have improved capability to deliver such a bifocal capability. Rather than intercepting regions of the global image and focusing them differently, a liquid crystal layer of the type depicted at 2300 may divide the light 2320 into two polarization components 2351 and 2341 across the entire visible window. As long as the ambient light 2320 does not have a polarization preference then the images should appear similarly as would be the case with either focal characteristic alone. In other exemplary embodiments, such an ophthalmic device may be paired with light sources that are projected with defined polarizations for different effects such as displaying information with a select polarization so that it is brought to the magnified image.

Liquid crystal displays may inherently provide such an ambient condition since light may emerge from such a display with a defined polarization characteristic. There may be many exemplary embodiments that result from the ability to leverage the devices with multiple focal characteristics.

In other exemplary embodiments, the ability to actively control the focus of the device may allow for devices with a range of bifocal conditions. A resting state or non-energized state may comprise a bifocal with one polarization unfocused and the other polarization focused on mid distances. On activation the mid-distance component may be further focused to near imaging if the lens is bistable, or a range of focal lengths in other embodiments. The bifocal characteristic may allow a user to perceive his distance environment simultaneously with a focused image regardless of how close it is, which may have advantages of various kinds. Any, of the liquid crystal embodiments where the liquid crystal layer may be oriented along a polarization dimension may comprise embodiments that may be useful for forming bifocal designs of this embodiment type.

In this description, reference has been made to elements illustrated in the figures. Many of the elements are depicted for reference to depict the exemplary embodiments of the inventive art for understanding. The relative scale of actual features may be significantly different from that as depicted, and variation from the depicted relative scales should be assumed within the spirit of the art herein. For example, liquid crystal molecules may be of a scale to be impossibly small to depict against the scale of insert pieces. The depiction of features that represent liquid crystal molecules at a similar scale to insert pieces to allow for representation of factors such as the alignment of the molecules is therefore such an example of a depicted scale that in actual embodiments may assume much different relative scale.

Although shown and described in what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An energized ophthalmic lens device comprising:
   a variable optic insert comprising at least a portion within the optical zone and comprising an insert front curve piece and an insert back curve piece, wherein a back surface of the front curve piece and a front surface of the back curve piece have differing surface topology at least in the portion within the optical zone, the variable optic insert further comprising a non-optical zone;
   an energy source embedded in the variable optic insert in at least a region comprising the non-optical zone; and
   a layer of liquid crystal material operatively associated with the variable optic insert.

2. The energized ophthalmic lens device of claim 1 wherein the ophthalmic lens device comprises a contact lens.

3. The energized ophthalmic lens device of claim 2, further comprising:
   a first layer of electrode material proximate to the back surface of the front curve piece; and
   a second layer of electrode material proximate to the front surface of the back curve piece.

4. The energized ophthalmic lens device of claim 3, further comprising a first layer of dielectric material proximate to the layer of liquid crystal material wherein the first layer of dielectric material varies in thickness across a region within the optical zone resulting in a varying electric field across the layer of liquid crystal material when an electric potential is applied across the first layer of electrode material and the second layer of electrode material.

5. The energized ophthalmic lens device of claim 3 wherein the layer of liquid crystal material varies its index of refraction affecting a ray of light traversing the layer of liquid crystal material when an electric potential is applied across the first layer of electrode material and the second layer of electrode material.

6. The energized ophthalmic lens device of claim 5 wherein the variable optic insert alters a focal characteristic of the lens.

7. The energized ophthalmic lens device of claim 6 further comprises a processor.

8. An energized ophthalmic lens device comprising:
   a variable optic insert comprising at least a portion within the optical zone, and comprising an insert front curve piece, an intermediate curve piece and an insert back curve piece, wherein a back surface of the front curve piece and a front surface of the intermediate curve piece have differing surface topology at least in the portion within the optical zone, the variable optic insert further comprising a non-optical zone;
   an energy source embedded in the variable optic insert in at least a region comprising the non-optical zone; and
   at least a first and second layer of liquid crystal material operatively associated with the variable optic insert.

9. The energized ophthalmic lens device of claim 8 wherein the ophthalmic lens device comprises a contact lens.

10. The energized ophthalmic lens device of claim 9 further comprising:
    a first layer of electrode material proximate to the back surface of the front curve piece;
    a second layer of electrode material proximate to the front surface of the intermediate curve piece; and
    wherein the first layer of liquid crystal material is between the first layer of electrode material and the second layer of electrode material.

11. The energized ophthalmic lens device of claim 10 further comprising a first layer of dielectric material proximate to the first layer of liquid crystal material wherein the first layer of dielectric material varies in thickness across a region within the optical zone resulting in a varying electric field across the layer of liquid crystal material when an electric potential is applied across the first layer of electrode material and the second layer of electrode material.

12. The energized ophthalmic lens device of claim 10 wherein the layer of first liquid crystal material varies its index of refraction affecting a ray of light traversing the first layer of liquid crystal material when an electric potential is applied across the first layer of electrode material and the second layer of electrode material.

13. The energized ophthalmic lens device of claim 10 wherein the variable optic insert alters a focal characteristic of the lens.

14. The energized ophthalmic lens device of claim 10 further comprises an electrical circuit, wherein the electrical circuit controls the flow of electrical energy from the energy source to the first and second electrode layers.

15. The energized ophthalmic lens device of claim 14 wherein the electrical circuit comprises a processor.

16. The energized ophthalmic lens device of claim 15 wherein the first liquid crystal layer is between and proximate to a first alignment layer and a second alignment layer, wherein the first and second alignment layers are collectively between the first layer of electrode material and the second layer of electrode material, and wherein the first layer of electrode material and the second layer of electrode material are in electrical communication with the electrical circuit.

17. The energized ophthalmic lens device of claim 16 further comprising:
- a third alignment layer and a forth alignment layer, wherein the second
- liquid crystal layer is between and proximate to the third alignment layer and the forth alignment layer;
- a third layer of electrode material and a forth layer of electrode material,
- wherein the second liquid crystal layer, the third alignment layer and the forth alignment layer are collectively between the third layer of electrode material; and
- wherein the third layer of electrode material and the forth layer of electrode material are in electrical communication with the electrical circuit.

18. The energized ophthalmic lens device of claim 17 wherein the first alignment layer and the second alignment layer align the first liquid crystal layer predominantly along a first linear axis; and the third alignment Lauer and the forth alignment layer align the second liquid crystal layer predominantly along a second linear axis.

19. The energized ophthalmic lens device of claim 18 wherein the first linear axis is approximately perpendicular to the second linear axis.

20. The energized ophthalmic lens device of claim 8 wherein the intermediate curve piece is a combination of two curved pieces which have been joined together.

21. An energized ophthalmic lens device comprising:
- a variable optic insert comprising at least a portion within the optical zone and comprising an insert front curve piece and an insert back curve piece, wherein a back surface of the front curve piece and a front surface of the back curve piece have differing surface topology at least in the portion within the optical zone, the variable optic insert further comprising a non-optical zone;
- an energy source embedded in the variable optic insert in at least a region comprising the non-optical zone;
- a single layer of aligned liquid crystal material operatively associated with the variable optic insert, wherein the single layer of aligned liquid crystal material interacts strongly with a first polarization orientation of incident light and not with a second polarization orientation of incident light, wherein the first polarization orientation of incident light is orthogonal to the second polarization orientation of incident light; and wherein the differential interaction of the single layer with the first polarization orientation of incident light forms a first focal characteristic different from a second focal characteristic determined by interaction of the single layer with the second polarization orientation of incident light.

* * * * *